United States Patent
Kara

(10) Patent No.: US 9,051,576 B2
(45) Date of Patent: Jun. 9, 2015

(54) METHYLOTROPHIC YEAST TRANSFORMED WITH GAL PROMOTERS

(75) Inventor: Bhupendra Vallabh Kara, Billingham (GB)

(73) Assignee: Fujifilm Diosynth Biotechnologies UK Limited, Billingham (GB)

( * ) Notice: Subject to any disclaimer, the term of this patent is extended or adjusted under 35 U.S.C. 154(b) by 0 days.

(21) Appl. No.: 14/237,021

(22) PCT Filed: Jul. 26, 2012

(86) PCT No.: PCT/GB2012/000616
§ 371 (c)(1),
(2), (4) Date: Feb. 4, 2014

(87) PCT Pub. No.: WO2013/017813
PCT Pub. Date: Feb. 7, 2013

(65) Prior Publication Data
US 2014/0162315 A1    Jun. 12, 2014

(30) Foreign Application Priority Data
Aug. 4, 2011   (GB) .................................. 1113419.4

(51) Int. Cl.
*C12P 21/02* (2006.01)
*C12N 15/81* (2006.01)
*C12P 21/00* (2006.01)

(52) U.S. Cl.
CPC ............... *C12N 15/815* (2013.01); *C12P 21/02* (2013.01); *C12P 21/00* (2013.01)

(58) Field of Classification Search
None
See application file for complete search history.

(56) References Cited

U.S. PATENT DOCUMENTS

| 5,912,154 | A  | * | 6/1999 | Ferro-Novick et al. | ........ 435/193 |
| 2003/0040047 | A1 | * | 2/2003 | Farwick et al. | ............. 435/69.1 |

FOREIGN PATENT DOCUMENTS

| EP | 0 174 585 | 3/1986 |
| EP | 2 546 340 | 1/2013 |
| JP | 06-078767 | 3/1994 |
| WO | 2011/099263 | 8/2011 |

OTHER PUBLICATIONS

Dominguez et al., Non-Conventional Yeasts as Hosts for Heterologous Protein Production, International Microbiology, 1, pp. 131-142 (1998).

* cited by examiner

*Primary Examiner* — Jim Ketter
(74) *Attorney, Agent, or Firm* — Morgan, Lewis & Bockius LLP

(57) ABSTRACT

A recombinant yeast of the genus *Komagataella* which has been transformed with a galactose promoter is provided. The yeast is preferably *Komagataella phaffii*, and the promoter is preferably a *S. cerevisiae* GAL1 or GAL10 promoter. Vectors and methods for producing recombinant polypeptides are also provided.

16 Claims, No Drawings

SEQUENCE LISTING

```
<160> NUMBER OF SEQ ID NOS: 11

<210> SEQ ID NO 1
<211> LENGTH: 858
<212> TYPE: DNA
<213> ORGANISM: Artificial Sequence
<220> FEATURE:
<223> OTHER INFORMATION: Modified gal promoter

<400> SEQUENCE: 1
gtgaaggccc atgaggccag ttaattaaga ggtaccatgc ataaagagct ccttagatct      60
```

```
gaacaattgg gggttttttc tccttgacgt taaagtatag aggtatatta acaattttt      120 gttgatactt ttattacatt tgaataagaa gtaaacaaaa ccgaaaatgt tgaaagtatt     180
agttaaagtg gttatgcagt ttttgcattt atatatctgt taatagatca aaaatcatcg     240
cttcgctgat taattacccc agaaataagg ctaaaaaact aatcgcatta tcatcctatg     300
gttgttaatt tgattcgttc atttgaaggt ttgtggggcc aggttactgc caattttcc      360 tcttcataac cataaaagct agtattgtag aatctttatt gttcggagca gtgcggcgcg     420
aggcacatct gcgtttcagg aacgcgaccg gtgaagacga ggacgcacgg aggagagtct     480
tccttcggag ggctgtcacc cgctcggcgg cttctaatcc gtacttcaat atagcaatga     540
gcagttaagc gtattactga aagttccaaa gagaaggttt ttttaggcta agataatggg     600
gctctttaca tttccacaac atataagtaa gattagatat ggataggaat tgtgagcgct     660
cacaattcct aatgccatgt aatatgatta ttaaacttct ttgcgtccat ccaaaaaaaa     720
agtaagaatt tttgaaaatt cgagttcaac cctcactaaa gggcggccat atgcaagtcg     780
actttggcgc gcctttgaat tcaaagcggc cgcttaggat ccaagcttta gagctcatgg     840
cgcgcctagg ccttgacg                                                    858

<210> SEQ ID NO 2
<211> LENGTH: 2071
<212> TYPE: DNA
<213> ORGANISM: Homo sapiens

<400> SEQUENCE: 2
ggcgcgccga attcaaaaat gagattccca tccatcttca ccgctgtttt gttcgctgct      60
tcttctgctt tagctgcccc agttaacact actactgagg acgagactgc tcaaattcca     120
gctgaggctg ttattggtta ctctgacttg gagggagatt tcgacgttgc tgtcttgcca     180
ttctccaact ccactaacaa cggactgctg ttcatcaaca ctactatcgc ttccattgcc     240
gctaaagaag agggagtttc tctcgagaag agagaagctg aagctatgga cgctcacaag     300
tctgaagttg cccacagatt caaggacttg ggtgaagaga acttcaaggc cttggttttg     360
attgctttcg cccagtactt gcaacaatgt ccattcgagg accacgttaa gttggttaac     420
gaggttaccg agttcgctaa gacttgtgtt gctgacgaat ccgctgaaaa ctgtgacaag     480
tccttgcaca ctttgttcgg tgacaagttg tgtactgtcg ctaccttgag agaaacctac     540
ggtgaaatgg ctgactgttg tgccaagcaa gaaccagaaa gaaacgagtg cttcttgcaa     600
cacaaggacg acaacccaaa cttgccaaga cttgtcagac cagaggttga cgttatgtgt     660
actgccttcc acgacaacga agagactttc ctgaagaagt acctgtacga gatcgctaga     720
agacacccat acttctacgc tccagagttg ttgttcttcg ccaagagata caaggctgct     780
ttcaccgaat gttgtcaggc tgctgataag gctgcttgct tgttgccaaa gttggacgag     840
ttgagagatg agggaaaggt ttcctctgcc aagcagagat tgaagtgtgc ttccctgcaa     900
aagttcggtg aaagagcttt taaggcttgg gctgttgcta gattgtccca gagattccca     960
aaggctgagt cgctgaggt ttccaagttg gttaccgact tgactaaggt tcacaccgag    1020
tgttgtcacg gtgacttgtt ggaatgtgct gatgacagag ctgacttggc taagtacatc    1080
tgtgaaaacc aggactccat ctcctctaag ttgaaagagt gctgcgagaa gccattgttg    1140
gagaagtccc actgtattgc tgaagttgag aacgacgaaa tgccagctga tttgccatct    1200
ttggctgctg acttcgttga atccaaggat gtctgcaaga actacgctga ggctaaggat    1260
```

```
gttttcctgg gaatgttctt gtacgagtac gccagaagac atccagacta ctccgtcgtc    1320
ttgttgttga gattggccaa gacttacgag actaccttgg agaagtgttg tgctgctgct    1380
gatccacatg agtgttacgc caaggttttc gacgagttca agccattggt tgaggaacca    1440
cagaacctga tcaagcagaa ctgtgagttg ttcgagcaac tgggtgagta caagttccag    1500
aacgccttgc ttgttagata caccaagaag gtcccacaag tttccactcc aaccttggtt    1560
gaggtttcca gaaacctggg taaagttggt tccaagtgct gtaagcaccc agaggctaag    1620
agaatgccat gtgccgaaga ttacttgtcc gttgtcttga accagttgtg tgtcttgcac    1680
gaaaagactc cagtttccga cagagttacc aagtgttgta ccgagtcctt ggtcaacaga    1740
agaccttgtt tctccgcttt ggaggttgac gaaacctacg tcccaaaaga gttcaacgct    1800
gagactttca ctttccacgc tgacatctgt actttgtccg agaaagagag acagatcaag    1860
aagcagactg ccttggttga attggtcaag cacaagccaa aggctactaa agagcagttg    1920
aaggctgtta tggatgactt cgctgctttc gttgagaagt gttgcaaggc tgacgacaaa    1980
gagacttgtt tcgccgaaga gggaaagaaa ttggttgctg cttcccaagc tgctttgggt    2040
ttgtagtagg cggccgcgga tccttaatta a                                   2071

<210> SEQ ID NO 3
<211> LENGTH: 3644
<212> TYPE: DNA
<213> ORGANISM: Artificial Sequence
<220> FEATURE:
<223> OTHER INFORMATION: AOX and resistance marker vector

<400> SEQUENCE: 3
ctgcagacta gtagatctaa catccaaaga cgaaaggttg aatgaaacct ttttgccatc      60
cgacatccac aggtccattc tcacacataa gtgccaaacg caacaggagg ggatacacta     120
gcagcagacc gttgcaaacg caggacctcc actcctcttc cctcaacac ccacttttgc      180 catcgaaaaa ccagcccagt tattgggctt gattggagct cgctcattcc aattccttct     240
attaggctac taacaccatg actttattag cctgtctatc ctggcccccc tggcgaggtt     300
catgtttgtt tatttccgaa tgcaacaagc tccgcattac acccgaacat cactccagat     360
gagggctttc tgagtgtggg gtcaaatagt ttcatgttcc ccaaatggcc caaaactgac     420
agtttaaacg ctgtccttgga acctaatatg acaaaagcgt gatctcatcc aagatgaact     480
aagtttggtt cgttgaaatg ctaacggcca gttggtcaaa agaaacttc caaaagtcgg      540 cataccgttt gtcttgtttg gtattgattg acgaatgctc aaaaataatc tcattaatgc     600
ttagcgcagt ctctctatcg cttctgaacc ccggtgcacc tgtgccgaaa cgcaaatggg     660
gaaacacccg cttttggat gattatgcat tgtctccaca ttgtatgctt ccaagattct      720
ggtgggaata ctgctgatag cctaacgttc atgatcaaaa tttaactgtt ctaaccccta     780
cttgacagca atatataaac agaaggaagc tgccctgtct aaaccttttt ttttatcat     840 cattattagc ttactttcat aattgcgact ggttccaatt gacaagcttt tgattttaac     900
gacttttaac gacaacttga gagaattcac gtggcccagc cggccgtcag atcaaaaaac     960
aactaattat tcgaaaaaat gagatttcct tcaatttta ctgctgtttt attcgcagca    1020
tcctccgcat tagctgctcc agtcaacact acaacagaag atgaaacggc acaaattccg    1080
gctgaagctg tcatcggtta ctcagattta gaaggggatt tcgatgttgc tgttttgcca    1140
ttttccaaca gcacaaataa cggggttattg tttataaata ctactattgc cagcattgct    1200
gctaaagaag aagggggtatc tctcgagaag cgctgtttgt agcctggtac cacgagccgc    1260
```

```
ggcggccgct agacatgact gttcctcagt tcaagttggg cacttacgag tagaccggtc      1320
ttgctagatt ctaatcaaga ggatgtcaga atgccatttg cctgagagat gcaggcttca      1380
tttttgatac ttttttattt gtaacctata tagtatagga ttttttttgt cattttgttt      1440
cttctcgtac gagcttgctc ctgatcagcc tatctcgcag ctgatgaata tcttgtggta      1500
ggggtttggg aaaatcattc gagtttgatg ttttttcttgg tatttcccac tcctcttcag     1560
agtacagaag attaagtgcg atcttcgttt gtgcggatcc cccacacacc atagcttcaa      1620
aatgtttcta ctccttttt actcttccag attttctcgg actccgcgca tcgccgtacc       1680
acttcaaaac acccaagcac agcatactaa attttccctc tttcttcctc tagggtgtcg      1740
ttaattaccc gtactaaagg tttggaaaag aaaaagaga tcgcctcgtt tcttttcctt       1800
cgtcgaaaaa ggcaataaaa attttatca cgtttctttt tcttgaaatt ttttttttta      1860 gttttttct ctttcagtga cctccattga tatttaagtt aataaacgga cttcaatttc       1920
tcaagtttca gtttcattt tcttgttcta ttacaacttt ttttacttct tgttcattag      1980
aaagaaagca tagcaatcta atctaagggg cggtgttgac aattaatcat cggcatagta      2040
tatcggcata gtataatacg acaaggtgag gaactaaacc atggccaagt tgaccagtgc      2100
cgttccggtg ctcaccgccc gtgacgtcgc cggagccgtc gagttctgga ccgaccgtct      2160
cgggttctcc cgtgacttcg tggaggacga cttcgccggt gtggtccgtg acgacgtgac      2220
cctgttcatc agcgccgtcc aggaccaggt ggtgccggac aacaccctgg cctgggtgtg      2280
ggtgcgtggc ctggacgagc tgtacgccga gtggtcggag gtcgtgtcca cgaacttccg      2340
tgacgcctcc gggccggcca tgaccgagat cggcgagcag ccgtgggggc gtgagttcgc      2400
cctgcgtgac ccggccggca actgcgtgca cttcgtggcc gaggagcagg actgacacgt      2460
ccgacggcgg cccacgggtc ccaggcctcg gagatccgtc cccttttcc tttgtcgata      2520 tcatgtaatt agttatgtca cgcttacatt cacgccctcc ccccacatcc gctctaaccg      2580
aaaaggaagg agttagacaa cctgaagtct aggtccctat ttattttttt atagttatgt      2640
tagtattaag aacgttattt atatttcaaa tttttctttt ttttctgtac agacgcgtgt      2700
acgcatgtaa cattatactg aaaaccttgc ttgagaaggt tttgggacgc tcgaaggctt      2760
taatttgcaa gctggtgagc agccttccgc ttcctcgctc actgactcgc tgcgctcggt      2820
cgttcggctg cggcgagcgg tatcagctca ctcaaaggcg gtaatacggt tatccacaga      2880
atcaggggat aacgcaggaa agaacatgtg agcaaaaggc cagcaaaagg ccaggaaccg      2940
taaaaaggcc gcgttgctgg cgttttttcca taggctccgc cccccctgacg agcatcacaa      3000 aaatcgacgc tcaagtcaga ggtggcgaaa cccgacagga ctataaagat accaggcgtt      3060
tccccctgga agctccctcg tgcgctctcc tgttccgacc ctgccgctta ccggatacct      3120
gtccgccttt ctcccttcgg gaagcgtggc gctttctcat agctcacgct gtaggtatct      3180
cagttcggtg taggtcgttc gctccaagct gggctgtgtg cacgaacccc ccgttcagcc      3240
cgaccgctgc gccttatccg gtaactatcg tcttgagtcc aacccggtaa gacacgactt      3300
atcgccactg gcagcagcca ctggtaacag gattagcaga gcgaggtatg taggcggtgc      3360
tacagagttc ttgaagtggt gggctaacta cggctacact agaagaacag tatttggtat      3420
ctgcgctctg ctgaagccag ttaccttcgg aaaaagagtt ggtagctctt gatccggcaa      3480
acaaaccacc gctggtagcg gtggttttt tgtttgcaag cagcagatta cgcgcagaaa      3540
aaaaggatct caagaagatc ctttgatctt ttctacgggg tctgacgctc agtggaacga      3600
```

```
cgcgcgcgta actcacgtta agggattttg gtcatgaggc tagc                3644

<210> SEQ ID NO 4
<211> LENGTH: 2069
<212> TYPE: DNA
<213> ORGANISM: Homo sapiens

<400> SEQUENCE: 4
ggcgcgccga attcaaaaat gagattccca tccatcttca ccgctgtttt gttcgctgct    60
tcttctgctt tagctgcccc agttaacact actactgagg acgagactgc tcaaattcca   120
gctgaggctg ttattggtta ctctgacttg gagggagatt tcgacgttgc tgtcttgcca   180
ttctccaact ccactaacaa cggactgctg ttcatcaaca ctactatcgc ttccattgcc   240
gctaaagaag agggagtttc tctcgagaag agagaagctg aagctatgga cgctcacaag   300
tctgaagttg cccacagatt caaggacttg ggtgaagaga acttcaaggc cttggttttg   360
attgctttcg cccagtattg caacaatgtc cattcgagga ccacgttaag ttggttaacg   420
aggttaccga gttcgctaag acttgtgttg ctgacgaatc cgctgaaaac tgtgacaagt   480
ccttgcacac tttgttcggt gacaagttgt gtactgtcgc taccttgaga gaaacctacg   540
gtgaaatggc tgactgttgt gccaagcaag aaccagaaaa aaacgagtgc ttcttgcaac   600
acaaggacga caacccaaac ttgccaagac ttgtcagacc agaggttgac gttatgtgta   660
ctgccttcca cgacaacgaa gagactttcc tgaagaagta cctgtacgag atcgctagaa   720
gacacccata cttctacgct ccagagttgt tgttcttcgc caagagatac aaggctgctt   780
tcaccgaatg ttgtcaggct gctgataagg ctgcttgctt gttgccaaag ttggacgagt   840
tgagagatga gggaaaggtt tcctctgcca agcagagatt gaagtgtgct tccctgcaaa   900
agttcggtga aagagctttt aaggcttggg ctgttgctag attgtcccag agattcccaa   960
aggctgagtt cgctgaggtt ccaagttggg ttaccgactt gactaaggtt cacaccgagt  1020
gttgtcacgg tgacttgttg gaatgtgctg atgacagagc tgacttggct aagtacatct  1080
gtgaaaacca ggactccatc tcctctaagt tgaaagagtg ctgcgagaag ccattgttgg  1140
agaagtccca ctgtattgct gaagttgaga acgacgaaat gccagctgat ttgccatctt  1200
tggctgctga cttcgttgaa tccaaggatg tctgcaagaa ctacgctgag gctaaggatg  1260
ttttcctggg aatgttcttg tacgagtacg ccagaagaca tccagactac tccgtcgtct  1320
tgttgttgag attggccaag acttacgaga ctaccttgga gaagtgttgt gctgctgctg  1380
atccacatga gtgttacgcc aagttttcga cgagttcaag ccattggttg aggaaccaca  1440
gaacctgatc aagcagaact gtgagttgtt cgagcaactg gtgagtaca agttccagaa  1500
cgccttgctt gttagataca ccaagaaggt cccacaagtt tccactccaa ccttggttga  1560
ggtttccaga aacctgggta agttggttc aagtgctgt aagcacccag aggctaagag  1620
aatgccatgt gccgaagatt acttgtccgt tgtcttgaac cagttgtgtg tcttgcacga  1680
aaagactcca gtttccgaca gagttaccaa gtgttgtacc gagtccttgg tcaacagaag  1740
accttgtttc tccgctttgg aggttgacga aacctacgtc ccaaaagagt caacgctga   1800
gactttcact ttccacgctg acatctgtac tttgtccgag aaagagagac agatcaagaa  1860
gcagactgcc ttggttgaat ggtcaagca aagccaaag gctactaaag agcagttgaa  1920
ggctgttatg gatgacttcg ctgctttcgt tgagaagtgt tgcaaggctg acgacaaaga  1980
gacttgttc gccgaagagg gaaagaaatt ggttgctgct tcccaagctg ctttgggttt  2040
gtagtaggcg gccgcggatc cttaattaa                                     2069
```

<210> SEQ ID NO 5
<211> LENGTH: 1875
<212> TYPE: DNA
<213> ORGANISM: Artificial Sequence
<220> FEATURE:
<223> OTHER INFORMATION: Synthetic E coli lacI gene

<400> SEQUENCE: 5

```
cgaattgaag gaaggccgtc aaggccgcat ttaattaagc cgcactgctc cgaacaataa      60
agattctaca atactagctt ttatggttat gaagaggaaa aattggcagt aacctggccc     120
cacaaacctt caaatgaacg aatcaaatta acaaccatag gatgataatg cgattagttt     180
tttagcctta tttctggggt aattaatcag cgaagcgatg attttttgatc tattaacaga    240
tatataaatg caaaaactgc ataaccactt taactaatac tttcaacatt ttcggttttgt    300
attacttctt attcaaatgt aataaaagta tcaacaaaaa attgttaata tacctctata    360
ctttaacgtc aaggagaaaa accccccaa ttgctgcaga aaatgaagc cagttacctt      420
gtacgacgtt gctgagtacg ctggtgtttc ctaccaaact gtttccagag ttgttaacca     480
ggcttctcac gtttctgcta agactagaga aaggttgaa gctgctatgg ctgagttgaa      540
ctacatccca aacagagttg ctcaacagtt ggctggtaag cagtccttgt tgatcggtgt     600
tgctacttct tctttggcct tgcacgctcc atctcaaatc gttgctgcta tcaagtccag     660
agctgaccag ttgggtgctt ccgttgttgt ttccatggtt gagagatccg gtgttgaggc     720
ttgtaaggct gctgttcaca acttgttggc tcagagagtt tccggtttga tcatcaacta    780
cccattggat gaccaagacg ctattgctgt tgaggctgct tgtacaaacg ttccagcttt     840
gttcttggac gtttccgacc aaactccaat caactccatc atcttctcac acgaggacgg     900
tactagattg ggtgttgagc acttggttgc tttgggtcac caacagatcg ctttgttggc     960
tggtccattg tcctctgttt ccgctagatt gagattggct ggttggcaca agtacttgac    1020
tagaaaccag atccagccta ttgctgaaag agagggagat tggtctgcta tgtccggttt    1080
ccaacagact atgcagatgt tgaacgaggg tatcgttcca actgctatgt tggttgctaa    1140
cgaccaaatg gctttgggtg ctatgagagc tattactgag tccggtttga gagttggtgc    1200
tgacatttcc gttgttggtt acgatgacac tgaggactcc tcttgttaca tcccaccatt    1260
gactactatc aagcaggact tcagactttt gggtcagact tccgttgaca gactgttgca    1320
gttgtcccag ggtcaagctg ttaagggtaa ccagttgttg ccagtttcct tggttaagag    1380
aaaagactac ttggctccaa acactcaaac tgcttcccca agagctttgg ctgactcctt    1440
gatgcagttg gctagacagg tttccagatt ggaatctggt caatcctctt tgaggcctag    1500
aaagagaaag aagtagtcta gagatcctgg tacgttcctc aaggtgctcg tgtctacacc    1560
gaaaaattcc aatgttctaa cgacacctac ctcagatacg tcattaacga tgctgttgtt    1620
ccaattcaaa cctgttccac tggtccaggg ttctcttgtg aaatcaatga cttctacgac    1680
tatgctgaaa agagagtagc cggtactgac ttcctaaagg tctgtaacgt cagcagcgtc    1740
agtaactcta ctgaattgac cttctactgg gactggaaca ctactcatta aacgccagt    1800
ctattgagac aatagttttg tataactaaa taatattggc gcgccctggg cctcatgggc   1860
cttccttcta ctgcc                                                     1875
```

<210> SEQ ID NO 6
<211> LENGTH: 744
<212> TYPE: DNA

<213> ORGANISM: Homo sapiens

<400> SEQUENCE: 6

```
gagcggaagg cccatgaggc cagttaatta agaggtaccc atatgtaata gaaaaatgaa      60
gtgggttact tttatttctt tgttgttctt gttttcatct gcttactcta gaggtgtttt     120
tagaagagat gctcataagt ctgaagttgc tcatagattc aaggatttgg gtgaagaaaa     180
ctttaaggct ttggttttga ttgcttttgc tcaatacttg caacaatctc catttgaaga     240
tcatgttaag ttggttaacg aagttactga atttgctaag acttgtgttg ctgatgaatc     300
tgctgaaaac tgtgataagt ctcttcatac tttgtttggt gataagttgt gtactgttgc     360
tactttgaga gaaacttacg gtgaaatggc tgactgttgt gctaagcaag aaccagaaag     420
aaacgaatgt ttcttgcaac ataaggatga taacccaaac ttgccaagat tggttagacc     480
tgaagttgat gttatgtgta ctgcttttca tgataacgaa gagacttttt tgaagaagta     540
cttgtacgaa attgctagaa gacatccata cttttacgct ccagagttgt tgttttttgc     600
taagagatac aaggctgctt ttactgaatg ttgtcaagct gctgataagg ctgcttgttt     660
gttgccaaag ttggatgaat tgagagatga aggaaaggtt tcttcgagct catggcgcgc     720
ctaggccttg acggccttcc gcca                                            744
```

<210> SEQ ID NO 7
<211> LENGTH: 4242
<212> TYPE: DNA
<213> ORGANISM: Artificial Sequence
<220> FEATURE:
<223> OTHER INFORMATION: Synthetic GAL4 gene

<400> SEQUENCE: 7

```
gagcggaagg cccatgaggc cagttaatta agaggtacca gatcttgttc gtaaacaaaa      60
ttgcgactat atcgatggcc acgaagtcat cttgaccagc acagagaact cacaccgaga     120
ctacgaaatt agccgtcttc gaaggaattg gctggtcagt caagttcga tccgatttcc      180
tttgagttta gtccgcctcc taaataaccc ggttattaac cgttaaatgg aaatggcacg     240
acacatacca ttaggcgggc caccagatat gagactttga cagtctaaac gctcacatcg     300
agtgcgccat aaatcttgaa atgattgaga gcagcatttc aattcattca cagccaatat     360
tcaccgataa tccatatcat taatctgaag gaagataatt cttggtcaat tcacgggatg     420
agtaagtcag gaaacggagc ttcgtcagta gtgggcaagt ttctaagtta ctacgggact     480
cttttccggta tggactgtgc ttctaagttt cgaggctcaa gatggagtac atcaaagtga     540
aaaaggcata cgatcctcgc tctctgtcag aatatttcaa ggctctaatg gagctgggca     600
gtttgggtga cgtggcagaa aactagacct gttgaactag cgagagagtt tggattagcg     660
ttttttcacg ggttgcttca agaacaactt gttgtactgg caattctaca cccaaaacaa     720
ctcaaaaatc caaaaacaca acttatctga cgcaggcata tacacccta aatccagcat     780
gcattttggc acaccagccg ccctttcat ttgcacgtc ttctccaaac tacgtgtgtt     840
ttatcggaat taactggaaa gatcacaggt tacgtaatac ctgtccgcga tcgcccgatc      900
tcatggctcc cacaagagcc aatcaaatcc cgcgaatttg aaatcggaac atgtaggaac      960
tcaattgtca tatataaata attcccttcc cgtggaaact gaaaaaaag ctcaccccga    1020
cttatttatt caatccaaca caaaaatgaa gctactgtct ctatcgaac aagcatgcga     1080
tatttgccga cttaaaaagc tcaagtgctc caaagaaaaa ccgaagtgcg ccaagtgtct     1140
gaagaacaac tgggagtgtc gctactctcc caaaaccaaa aggtctccgc tgactagggc     1200
```

```
acatctgaca gaagtggaat caaggctaga aagactggaa cagctatttc tactgatttt    1260
tcctcgagaa gaccttgaca tgattttgaa aatggattct ttacaggata taaaagcatt    1320
gttaacagga ttatttgtac aagataatgt gaataaagat gccgtcacag atagattggc    1380
ttcagtggag actgatatgc ctctaacatt gagacagcat agaataagtg cgacatcatc    1440
atcggaagag agtagtaaca aaggtcaaag acagttgact gtatcgattg actcggcagc    1500
tcatcatgat aactccacaa ttccgttgga ttttatgccc agggatgctc ttcatggatt    1560
tgattggtct gaagaggatg acatgtcgga tggcttgccc ttcctgaaaa cggaccccaa    1620
caataatggg ttctttggcg acggttctct cttatgtatt cttcgatcta ttggctttaa    1680
accggaaaat tacacgaact ctaacgttaa caggctcccg accatgatta cggatagata    1740
cacgttggct tctagatcca caacatcccg tttacttcaa agttatctca ataattttca    1800
cccctactgc cctatcgtgc actcaccgac gctaatgatg ttgtataata accagattga    1860
aatcgcgtcg aaggatcaat ggcaaatcct ttttaactgc atattagcca ttggagcctg    1920
gtgtatagag ggggaatcta ctgatataga tgttttttac tatcaaaatg ctaaatctca    1980
tttgacgagc aaggtcttcg agtcaggttc cataattttg gtgacagccc tacatcttct    2040
gtcgcgatat acacagtgga ggcagaaaac aaatactagc tataatttc acagcttttc    2100
cataagaatg gccatatcat tgggcttgaa tagggacctc ccctcgtcct tcagtgatag    2160
cagcattctg gaacaaagac gccgaatttg gtggtctgtc tactcttggg agatccaatt    2220
gtccctgctt tatggtcgat ccatccagct ttctcagaat acaatctcct tcccttcttc    2280
tgtcgacgat gtgcagcgta ccacaacagg tcccaccata tatcatggca tcattgaaac    2340
agcaaggctc ttacaagttt tcacaaaaat ctatgaacta gacaaaacag taactgcaga    2400
aaaaagtcct atatgtgcaa aaaaatgctt gatgatttgt aatgagattg aggaggtttc    2460
gagacaggca ccaaagtttt tacaaatgga tatttccacc accgctctaa ccaatttgtt    2520
gaaggaacac ccttggctat cctttacaag attcgaactg aagtggaaac agttgtctct    2580
tatcatttat gtattaagag attttttcac taatttttacc cagaaaaagt cacaactaga    2640
acaggatcaa aatgatcatc aaagttatga agttaaacga tgctccatca tgttaagcga    2700
tgcagcacaa agaactgtta tgtctgtaag tagctatatg gacaatcata atgtcacccc    2760
atattttgcc tggaattgtt cttattactt ggtcaatgca gtcctagtac ccataaagac    2820
tctactctca aactcaaaat cgaatgctga gaataacgag accgcacaat tattacaaca    2880
aattaacact gttctgatgc tattaaaaaa actggccact tttaaaatcc agacttgtga    2940
aaaatacatt caagtactgg aagaggtatg tgcgccgttt ctgttatcac agtgtgcaat    3000
cccattaccg catatcagtt ataacaatag taatggtagc gccattaaaa atattgtcgg    3060
ttctgcaact atcgcccaat accctactct tccggaggaa aatgtcaaca atatcagtgt    3120
taaatatgtt tctctggctc agtagggcct tcacctgtgc cattgaaatc aggagcaagt    3180
ttcagtgatc tagtcaagct gttatctaac cgtccaccct ctcgtaactc tccagtgaca    3240
ataccaagaa gcacaccttc gcatcgctca gtcacgcctt ttctagggca acagcaacag    3300
ctgcaatcat tagtgccact gaccccgtct gctttgtttg gtggcgccaa ttttaatcaa    3360
agtgggaata ttgctgatag ctcattgtcc ttcactttca ctaacagtag caacggtccg    3420
aacctcataa caactcaaac aaattctcaa gcgcttttcac aaccaattgc ctcctctaac    3480
gttcatgata acttcatgaa taatgaaatc acggctagta aaattgatga tggtaataat    3540
```

| | |
|---|---|
| tcaaaaccac tgtcacctgg ttggacggac caaactgcgt ataacgcgtt tggaatcact | 3600 |
| acagggatgt ttaataccac tacaatggat gatgtatata actatctatt cgatgatgaa | 3660 |
| gatacccac caaacccaaa aaaagagtaa aatgagttta cgaatacttt agacaaattg | 3720 |
| gtttttattt gtatatagct aggtaaaaga ccgatcgaaa agaggcacgc tttgtaggtt | 3780 |
| taacgaagtt atttatttat ttactggagt attccactgg atgtaaactg gtctacttta | 3840 |
| atttggcatc catgccagcc ggacaagaaa aagaaacga gttagggatg taagatgtac | 3900 |
| gaggtcagat gtcggatgga ggcttgtttc ctacctcacg gtcccccacc ccctcctcca | 3960 |
| tcctttatct gctgagtact gactctcctc acaaaatctc attctgaaat tcgttagtaa | 4020 |
| ctacatcccc caagcattta caagtttgta cagtacggct acgaagttga cggaaaatgg | 4080 |
| atcaagatga tcttttcccg aatggtggta atccatcatc tagctccttg cctgacagta | 4140 |
| ccagcttgcg gtctgtagat actgaactgg ttcaagaagt cctggaggca actgagcggc | 4200 |
| cgcgagctca tggcgcgcct aggccttgac ggccttccgc ca | 4242 |

<210> SEQ ID NO 8
<211> LENGTH: 1044
<212> TYPE: DNA
<213> ORGANISM: Artificial Sequence
<220> FEATURE:
<223> OTHER INFORMATION: Synthetic kanamycin resistance gene

<400> SEQUENCE: 8

| | |
|---|---|
| gagcggaagg cccatgaggc cagttaatta agaggtaccc catgggcagc catattcaac | 60 |
| gggaaacgtc ttgctctagg ccgcgattaa attccaacat ggatgctgat ttatatgggt | 120 |
| ataaatgggc tcgcgataat gtcgggcaat caggtgcgac aatctatcga ttgtatggga | 180 |
| agcccgatgc gccagagttg tttctgaaac atggcaaagg tagcgttgcc aatgatgtta | 240 |
| cagatgagat ggtcagacta aactggctga cggaatttat gcctcttccg accatcaagc | 300 |
| attttatccg tactcctgat gatgcatggt tactcaccac tgcgatcccc gggaaaacag | 360 |
| cattccaggt attagaagaa tatcctgatt caggtgaaaa tattgttgat gcgctggcag | 420 |
| tgttcctgcg ccggttgcat tcgattcctg tttgtaattg tccttttaac agcgatcgcg | 480 |
| tatttcgtct cgctcaggcg caatcacgaa tgaataacgg tttggttgat gcgagtgatt | 540 |
| ttgatgacga gcgtaatggc tggcctgttg aacaagtctg gaaagaaatg cataagtttt | 600 |
| tgccattctc accggattca gtcgtcactc atggtgattt ctcacttgat aaccttattt | 660 |
| ttgacgaggg gaaattaata ggttgtattg atgttggacg agtcggaatc gcagaccgat | 720 |
| accaggatct tgccatccta tggaactgcc tcggtgagtt ttccacgtcc gacggcggcc | 780 |
| cacgggtccc aggcctcgga gatccgtccc ccttttcctt tgtcgatatc atgtaattag | 840 |
| ttatgtcacg cttacattca cgccctcccc cacatccgc tctaaccgaa aaggaaggag | 900 |
| ttagacaacc tgaagtctag gtccctattt attttttat agttatgtta gtattaagaa | 960 |
| cgttatttat atttcaaatt tttcttttt ttctgtacag acgctgagct catggcgcgc | 1020 |
| ctaggccttg acggccttcc gcca | 1044 |

<210> SEQ ID NO 9
<211> LENGTH: 8261
<212> TYPE: DNA
<213> ORGANISM: Artificial Sequence
<220> FEATURE:
<223> OTHER INFORMATION: Vector pAVE345

<400> SEQUENCE: 9

-continued

```
gacgaaaggg cctcgtgata cgcctatttt tataggttaa tgtcatgata ataatggttt    60
cttagacgtc aggtggcact tttcggggaa atgtgcgcgg aacccctatt tgtttatttt   120
tctaaataca ttcaaatatg tatccgctca tgagacaata accctgataa atgcttcaat   180
aatattgaaa aaggaagagt atgagtattc aacatttccg tgtcgccctt attccctttt   240
ttgcggcatt ttgccttcct gttttttgctc acccagaaac gctggtgaaa gtaaaagatg   300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
gcatgacagt aagagaatta tgcagtgctg ccataaccat gagtgataac actgcggcca   600
acttacttct gacaacgatc ggaggaccga aggagctaac cgcttttttg cacaacatgg   660
gggatcatgt aactcgcctt gatcgttggg aaccggagct gaatgaagcc ataccaaacg   720
acgagcgtga caccacgatg cctgtagcaa tggcaacaac gttgcgcaaa ctattaactg   780
gcgaactact tactctagct tcccggcaac aattaataga ctggatggag gcggataaag   840
ttgcaggacc acttctgcgc tcggcccttc cggctggctg gtttattgct gataaatctg   900
gagccggtga gcgtgggtct cgcggtatca ttgcagcact ggggccagat ggtaagccct   960
cccgtatcgt agttatctac acgacgggga gtcaggcaac tatggatgaa cgaaatagac  1020
agatcgctga gataggtgcc tcactgatta agcattggta actgtcagac caagtttact  1080
catatatact ttagattgat ttaaaacttc attttttaatt taaaaggatc taggtgaaga  1140
tcctttttga taatctcatg accaaaatcc cttaacgtga gttttcgttc cactgagcgt  1200
cagacccccgt agaaaagatc aaaggatctt cttgagatcc ttttttttctg cgcgtaatct  1260
gctgcttgca acaaaaaaa ccaccgctac cagcggtggt ttgtttgccg gatcaagagc  1320
taccaactct ttttccgaag gtaactggct tcagcagagc gcagatacca aatactgtcc  1380
ttctagtgta gccgtagtta ggccaccact tcaagaactc tgtagcaccg cctacatacc  1440
tcgctctgct aatcctgtta ccagtggctg ctgccagtgg cgataagtcg tgtcttaccg  1500
ggttggactc aagacgatag ttaccggata aggcgcagcg tcgggctga acggggggtt  1560
cgtgcacaca gcccagcttg gagcgaacga cctacaccga actgagatac ctacagcgtg  1620
agctatgaga aagcgccacg cttcccgaag ggagaaaggc ggacaggtat ccggtaagcg  1680
gcagggtcgg aacaggagag cgcacgaggg agcttccagg gggaaacgcc tggtatcttt  1740
atagtcctgt cgggtttcgc cacctctgac ttgagcgtcg attttttgtga tgctcgtcag  1800
gggggcggag cctatggaaa aacgccagca acgcggcctt tttacggttc ctggccttt   1860
gctggccttt tgctcacatg ctgggcccag ccggccagat cttgttcgta aacaaaattg  1920
cgactatatc gatggccacg aagtcatctt gaccagcaca gagaactcac accgagacta  1980
cgaaattagc cgtcttcgaa aggaattggc tggtcagtca agttcgatcc gatttccttt  2040
gagtttagtc cgcctcctaa ataacccggt tattaaccgt taaatggaaa tggcacgaca  2100
cataccatta ggcgggccac cagatatgag actttgacag tctaaacgct cacatcgagt  2160
gcgccataaa tcttgaaatg attgagagca gcatttcaat tcattcacag ccaatattca  2220
ccgataatcc atatcattaa tctgaaggaa gataattctt ggtcaattca cgggatgagt  2280
aagtcaggaa acggagcttc gtcagtagtg ggcaagtttc taagttacta cgggactctt  2340
```

-continued

```
tccggtatgg actgtgcttc taagtttcga ggctcaagat ggagtacatc aaagtgaaaa    2400
aggcatacga tcctcgctct ctgtcagaat atttcaaggc tctaatggag ctgggcagtt    2460
tgggtgacgt ggcagaaaac tagacctgtt gaactagcga gagagtttgg attagcgttt    2520
tttcacgggt tgcttcaaga acaacttgtt gtactggcaa ttctacaccc aaaacaactc    2580
aaaaatccaa aaacacaact tatctgacgc aggcatatac acccctaaat ccagcatgca    2640
ttttggcaca ccagccgccc ttttcatttg acacgtcttc tccaaactac gtgtgtttta    2700
tcggaattaa ctggaaagat cacaggttac gtaatacctg tccgcgatcg cccgatctca    2760
tggctcccac aagagccaat caaatcccgc gaatttgaaa tcggaacatg taggaactca    2820
attgtcatat ataaataatt cccttcccgt ggaaactgaa aaaaaagctc accccgactt    2880
atttattcaa tccaacacaa aaatgaagct actgtcttct atcgaacaag catgcgatat    2940
ttgccgactt aaaaagctca agtgctccaa agaaaaaccg aagtgcgcca agtgtctgaa    3000
gaacaactgg gagtgtcgct actctcccaa aaccaaaagg tctccgctga ctagggcaca    3060
tctgacagaa gtggaatcaa ggctagaaag actggaacag ctatttctac tgattttccc    3120
tcgagaagac cttgacatga ttttgaaaat ggattcttta caggatataa aagcattgtt    3180
aacaggatta tttgtacaag ataatgtgaa taaagatgcc gtcacagata gattggcttc    3240
agtggagact gatatgcctc taacattgag acagcataga ataagtgcga catcatcatc    3300
ggaagagagt agtaacaaag gtcaaagaca gttgactgta tcgattgact cggcagctca    3360
tcatgataac tccacaattc cgttggattt tatgcccagg gatgctcttc atggatttga    3420
ttggtctgaa gaggatgaca tgtcggatgg cttgcccttc ctgaaaacgg accccaacaa    3480
taatgggttc tttggcgacg gttctctctt atgtattctt cgatctattg gctttaaacc    3540
ggaaaattac acgaactcta acgttaacag gctcccgacc atgattacgg atagatacac    3600
gttggcttct agatccacaa catcccgttt acttcaaagt tatctcaata attttcaccc    3660
ctactgccct atcgtgcact caccgacgct aatgatgttg taataaacc agattgaaat     3720
cgcgtcgaag gatcaatggc aaatccttt taactgcata ttagccattg gagcctggtg     3780
tatagagggg gaatctactg atatagatgt tttttactat caaaatgcta atctcatttt    3840
gacgagcaag gtcttcgagt caggttccat aattttggtg acagccctac atcttctgtc    3900
gcgatataca cagtggaggc agaaaacaaa tactagctat aattttcaca gcttttccat    3960
aagaatggcc atatcattgg gcttgaatag ggacctcccc tcgtccttca gtgatagcag    4020
cattctggaa caaagacgcc gaatttggtg gtctgtctac tcttgggaga tccaattgtc    4080
cctgctttat ggtcgatcca tccagctttc tcagaataca atctccttcc cttcttctgt    4140
cgacgatgtg cagcgtacca caacaggtcc caccatatat catggcatca ttgaaacagc    4200
aaggctctta caagttttca caaaaatcta tgaactagac aaaacagtaa ctgcagaaaa    4260
aagtcctata tgtgcaaaaa aatgcttgat gatttgtaat gagattgagg aggtttcgag    4320
acaggcacca aagttttac aaatggatat ttccaccacc gctctaacca atttgttgaa     4380
ggaacaccct tggctatcct ttacaagatt cgaactgaag tggaaacagt tgtctcttat    4440
catttatgta ttaagagatt ttttcactaa ttttacccag aaaaagtcac aactagaaca    4500
ggatcaaaat gatcatcaaa gttatgaagt taaacgatgc tccatcatgt taagcgatgc    4560
agcacaaaga actgttatgt ctgtaagtag ctatatggac aatcataatg tcaccccata    4620
ttttgcctgg aattgttctt attacttgtt caatgcagtc ctagtaccca taagagactct   4680
actctcaaac tcaaaatcga atgctgagaa taacgagacc gcacaattat tacaacaaat    4740
```

-continued

```
taacactgtt ctgatgctat taaaaaaact ggccacttttt aaaatccaga cttgtgaaaa    4800
atacattcaa gtactggaag aggtatgtgc gccgtttctg ttatcacagt gtgcaatccc    4860
attaccgcat atcagttata acaatagtaa tggtagcgcc attaaaaata ttgtcggttc    4920
tgcaactatc gcccaatacc ctactcttcc ggaggaaaat gtcaacaata tcagtgttaa    4980
atatgtttct cctggctcag tagggccttc acctgtgcca ttgaaatcag gagcaagttt    5040
cagtgatcta gtcaagctgt tatctaaccg tccaccctct cgtaactctc cagtgacaat    5100
accaagaagc acaccttcgc atcgctcagt cacgcctttt ctagggcaac agcaacagct    5160
gcaatcatta gtgccactga ccccgtctgc tttgtttggt ggcgccaatt ttaatcaaag    5220
tgggaatatt gctgatagct cattgtcctt cactttcact aacagtagca acggtccgaa    5280
cctcataaca actcaaacaa attctcaagc gctttcacaa ccaattgcct cctctaacgt    5340
tcatgataac ttcatgaata atgaaatcac ggctagtaaa attgatgatg gtaataattc    5400
aaaaccactg tcacctggtt ggacggacca aactgcgtat aacgcgtttg gaatcactac    5460
agggatgttt aataccacta caatggatga tgtatataac tatctattcg atgatgaaga    5520
tacccccacca aacccaaaaa aagagtaaaa tgagtttacg aatactttag acaaattggt    5580
ttttatttgt atatagctag gtaaaagacc gatcgaaaag aggcacgctt tgtaggttta    5640
acgaagttat ttatttattt actggagtat tccactggat gtaaactggt ctactttaat    5700
ttggcatcca tgccagccgg acaagaaaaa agaaacgagt tagggatgta agatgtacga    5760
ggtcagatgt cggatggagg cttgtttcct acctcacggt ccccccacccc ctcctccatc    5820
ctttatctgc tgagtactga ctctcctcac aaaatctcat tctgaaattc gttagtaact    5880
acatccccca agcatttaca agtttgtaca gtacggctac gaagttgacg aaaatggat     5940
caagatgatc ttttcccgaa tggtggtaat ccatcatcta gctccttgcc tgacagtacc    6000
agcttgcggt ctgtagatac tgaactggtt caagaagtcc tggaggcaac tgagcggccg    6060
cgatatcgct agctcgagcc cacacaccat agcttcaaaa tgtttctact cctttttttac   6120
tcttccagat tttctcggac tccgcgcatc gccgtaccac ttcaaaacac ccaagcacag    6180
catactaaat ttcccctctt tcttcctcta gggtgtcgtt aattaccccgt actaaaggtt    6240
tggaaaagaa aaaagagacc gcctcgtttc ttttttcttcg tcgaaaaagg caataaaaat    6300
ttttatcacg tttcttttttc ttgaaaattt tttttttttag tttttttctc tttcgatgac    6360
ctcccattga tatttaagtt aataaacggt cttcaatttc tcaagtttca gtttcatttt    6420
tcttgttcta ttacaacttt ttttacttct tgctcattag aaagaaagca tagcaatcta    6480
atctaagggc ggcgttgaca attaatcatc ggcatagtat atcggcatag tataatacga    6540
caaggtgagg aactaaaacca tgggcagcca tattcaacgg gaaacgtctt gctctaggcc    6600
gcgattaaat tccaacatgg atgctgattt atatgggtat aaatgggctc gcgataatgt    6660
cgggcaatca ggtgcgacaa tctatcgatt gtatgggaag cccgatgcgc cagagttgtt    6720
tctgaaacat ggcaaaggta gcgttgccaa tgatgttaca gatgagatgg tcagactaaa    6780
ctggctgacg gaatttatgc ctcttccgac catcaagcat tttatccgta ctcctgatga    6840
tgcatggtta ctcaccactg cgatccccgg gaaaacagca ttccaggtat tagaagaata    6900
tcctgattca ggtgaaaata ttgttgatgc gctggcagtg ttcctgcgcc ggttgcattc    6960
gattcctgtt gtgtaattgtc cttttaacag cgatcgcgta tttcgtctcg ctcaggcgca    7020
atcacgaatg aataacggtt tggttgatgc gagtgatttt gatgacgagc gtaatggctg    7080
```

| | | |
|---|---|---|
| gcctgttgaa caagtctgga agaaatgca taagttttg ccattctcac cggattcagt | 7140 | |
| cgtcactcat ggtgatttct cacttgataa ccttattttt gacgagggga aattaatagg | 7200 | |
| ttgtattgat gttggacgag tcggaatcgc agaccgatac caggatcttg ccatcctatg | 7260 | |
| gaactgcctc ggtgagtttt ccacgtccga cggcggccca cgggtcccag gcctcggaga | 7320 | |
| tccgtccccc ttttcctttg tcgatatcat gtaattagtt atgtcacgct tacattcacg | 7380 | |
| ccctcccccc acatccgctc taaccgaaaa ggaaggagtt agacaacctg aagtctaggt | 7440 | |
| ccctatttat ttttttatag ttatgttagt attaagaacg ttatttatat ttcaaatttt | 7500 | |
| tcttttttt ctgtacagac gcgtgagcct cggagatccg tcccccttt cctttgtcga | 7560 | |
| tatcatgtaa ttagttatgt cacgcttaca ttcacgcccct cccccacat ccgctctaac | 7620 | |
| cgaaaaggaa ggagttagac aacctgaagt ctaggtccct atttattttt ttatagttat | 7680 | |
| gttagtatta agaacgttat ttatatttca aatttttctt ttttttctgt acagacgcgt | 7740 | |
| gtacgcatgt aacattatac tgaaaacctt gcttgagaag gttttgggac gctcgaaggc | 7800 | |
| tttaatttgc aagctgaatt cccggggatc tctagagtc gacctgcagg catgcaagct | 7860 | |
| tggcactggc cgtcgtttta caacgtcgtg actgggaaaa ccctggcgtt acccaactta | 7920 | |
| atcgccttgc agcacatccc cctttcgcca gctggcgtaa tagcgaagag gcccgcaccg | 7980 | |
| atcgcccttc ccaacagttg cgcagcctga tggcgaatg gcgcctgatg cggtattttc | 8040 | |
| tccttacgca tctgtgcggt atttcacacc gcatatatgg tgcactctca gtacaatctg | 8100 | |
| ctctgatgcc gcatagttaa gccagccccg acacccgcca cacccgctg acgcgccctg | 8160 | |
| acgggcttgt ctgctcccgg catccgctta cagacaagct gtgaccgtct ccgggagctg | 8220 | |
| catgtgtcag aggttttcac cgtcatcacc gaaacgcgcg a | 8261 | |

<210> SEQ ID NO 10
<211> LENGTH: 1685
<212> TYPE: DNA
<213> ORGANISM: Artificial Sequence
<220> FEATURE:
<223> OTHER INFORMATION: Synthetic kanamycin resistance gene

<400> SEQUENCE: 10

| | | |
|---|---|---|
| gctagcggtg tcctcgtcca atcaggtagc catctctgaa atatctggct ccgttgcaac | 60 | |
| tccgaacgac ctgctggcaa cgtaaaattc tccggggtaa aacttaaatg tggagtaatg | 120 | |
| gaaccagaaa cgtctcttcc cttctctctc cttccaccgc ccgttaccgt ccctaggaaa | 180 | |
| ttttactctg ctggagagct tcttctacgg cccccttgca gcaatgctct tcccagcatt | 240 | |
| acgttgcggg taaaacggag gtcgtgtacc cgacctagca gcccagggat ggaaaagtcc | 300 | |
| cggccgtcgc tggcaataat agcgggcgga cgcatgtcat gagattattg gaaaccacca | 360 | |
| gaatcgaata taaaaggcga acacctttcc caattttggt ttctcctgac ccaaagactt | 420 | |
| taaatttaat ttatttgtcc ctatttcaat caattgaaca actatttcga acgagcaat | 480 | |
| tcttatgagc catattcaac gggaaacgtc ttgctcgagg ccgcgattaa attccaacat | 540 | |
| ggatgctgat ttatatgggt ataaatgggc tcgcgataat gtcgggcaat caggtgcgac | 600 | |
| aatctatcga ttgtatggga agcccgatgc gccagagttg tttctgaaac atggcaaagg | 660 | |
| tagcgttgcc aatgatgtta cagatgagat ggtcagacta aactggctga cggaatttat | 720 | |
| gcctcttccg accatcaagc attttatccg tactcctgat gatgcatggt tactcaccac | 780 | |
| tgcgatcccc gggaaaacag cattccaggt attagaagaa tatcctgatt caggtgaaaa | 840 | |
| tattgttgat gcgctggcag tgttcctgcg ccggttgcat tcgattcctg tttgtaattg | 900 | |

```
tccttttaac agcgatcgcg tatttcgtct cgctcaggcg caatcacgaa tgaataacgg    960
tttggttgat gcgagtgatt ttgatgacga gcgtaatggc tggcctgttg aacaagtctg   1020
gaaagaaatg cataaacttt tgccattctc accggattca gtcgtcactc atggtgattt   1080
ctcacttgat aaccttattt ttgacgaggg gaaattaata ggttgtattg atgttggacg   1140
agtcggaatc gcagaccgat accaggatct tgccatccta tggaactgcc tcggtgagtt   1200
ttctccttca ttacagaaac ggcttttttca aaaatatggt attgataatc ctgatatgaa   1260
taaattgcag tttcatttga tgctcgatga gttttttctaa gcggccgcca gctttctaga   1320
acaaaaactc atctcagaag aggatctgaa tagcgccgtc gaccatcatc atcatcatca   1380
ttgagtttta gccttagaca tgactgttcc tcagttcaag ttgggcactt acgagaagac   1440
cggtcttgct agattctaat caagaggatg tcagaatgcc atttgcctga gatgcagg    1500 cttcattttt gatactttt tatttgtaac ctatatagta taggattttt tttgtcattt    1560
tgtttcttct cgtacgagct tgctcctgat cagcctatct cgcagctgat gaatatcttg   1620
tggtaggggt ttgggaaaat cattcgagtt tgatgttttt cttggtatttt cccactcctg   1680 aattc                                                               1685

<210> SEQ ID NO 11
<211> LENGTH: 2166
<212> TYPE: DNA
<213> ORGANISM: Artificial Sequence
<220> FEATURE:
<223> OTHER INFORMATION: Synthetic Mig1 gene

<400> SEQUENCE: 11
ggatcctttt ttgtagaaat gtcttggtgt cctcgtccaa tcaggtagcc atctctgaaa     60
tatctggctc cgttgcaact ccgaacgacc tgctggcaac gtaaaattct ccggggtaaa    120
acttaaatgt ggagtaatgg aaccagaaac gtctcttccc ttctctctcc ttccaccgcc    180
cgttaccgtc cctaggaaat tttactctgc tggagagctt cttctacggc ccccttgcag    240
caatgctctt cccagcatta cgttgcgggt aaaacggagg tcgtgtaccc gacctagcag    300
cccagggatg gaaaagtccc ggccgtcgct ggcaataata gcgggcggac gcatgtcatg    360
agattattgg aaaccaccag aatcgaatat aaaaggcgaa cacctttccc aattttggtt    420
tctcctgacc caaagacttt aaatttaatt tatttgtccc tatttcaatc aattgaacaa    480
cggcgcgcct taattaaaaa aaatggaaca aaaactcatc tcagaagagg atctgcaaag    540
cccatatcca atgacacaag tgtctaacgt tgatgatggg tcactattga aggagagtaa    600
aagcaagtcc aaagtagctg cgaagtcaga ggcgccaaga ccacatgctt gtcctatctg    660
tcatagagct tttcacagac tggaacatca gacgagacac atgagaattc atacaggtga    720
gaagcctcac gcgtgtgact ccccggatg tgtgaaaagg ttcagtagaa gcgatgaact    780
gacgagacac agaagaattc atacaaactc ccaccctcga ggtaaaagag cagaaagaa    840 gaaggttgtg ggctctccaa taaatagtgc tagttctagt gctaccagta taccagattt    900
aaatacggca aatttttcac cgccattacc acagcaacac ctatcgcctt taattccttat    960 tgctattgct ccgaaagaaa attcaagtcg atcttctaca agaaaggta gaaaaaccaa   1020 attcgaaatc ggcgaaagtg gtgggaatga cccatatatg gtttcttctc ccaaaacgat   1080
ggctaagatt cccgtctcgg tgaagcctcc accttcttta gcactgaata atatgaacta   1140
ccaaacttca tccgcttcca ctgctttgtc ttcgttgagc aatagccata gtggcagtag   1200
```

```
-continued actgaaactg aacgcgttat cgtccctaca aatgatgacg cccattgcta gcagtgcgcc   1260
aaggactgtt ttcatagacg gtcctgaaca gaaacaacta caacaacaac aaaattctct   1320
ttcaccacgt tattccaaca ctgttatatt accaaggccg cgatctttaa cggattttca   1380
aggattgaac aatgcaaatc caaacaacaa tggaagtctc agagcacaaa ctcagagttc   1440
cgtacagttg aagagaccaa gttcagtttt aagtttgaac gacttgttgg ttggccaaag   1500
aaataccaac gaatctgact ctgattttac tactggtggt gaggatgaag aagacggact   1560
aaaggacccg tctaactcta gtatcgataa ccttgagcaa gactatttgc aagagcaatc   1620
aagaaagaaa tctaagactt ccacgcccac gacaatgcta agtagatcca ctagtggtac   1680
gaatttgcac actttggggt atgtaatgaa ccaaaatcac ttgcatttct cctcatcatc   1740
tcctgatttc caaaggagt tgaacaacag attactgaac gttcaacaac agcagcaaga   1800
gcaacatacc ctactgcaat cacaaaatac gtcaaaccaa agtcaaaatc aaaatcaaaa   1860
tcaaatgatg gcttccagta gttcgttaag tacaacccccg ttattattgt caccaagggt   1920
gaatatgatt aatactgcta tatccaccca acaaaccccc atttctcagt cggattcaca   1980
agttcaagaa ctggaaacat taccacccat aagaagttta ccgttgccct tcccacacat   2040
ggactgatac gctgacaagt ttttggcggt gcagataaat caaaagacaa tagacaagaa   2100
ttaataatat taacaattaa taattaataa ataataaata ataataataa taataataat   2160
aagctt                                                               2166
```

METHYLOTROPHIC YEAST TRANSFORMED WITH GAL PROMOTERS

SEQUENCE LISTING SUBMISSION VIA EFS-WEB

A computer readable text file, entitled "056258-5153_SequenceListing.txt," created on or about 4 Feb. 2014, with a file size of about 39 kb contains the sequence listing for this application and is hereby incorporated by reference in its entirety.

The present invention concerns yeast strains and methods for the expression of polypeptides in yeasts.

Yeast species that assimilate methanol as a carbon source form a distinct proportion of all known yeasts. The classification/renaming of these yeasts has underdone a number of changes recently (for reviews see C. P. Kurtzman, International Journal of Systematic and Evolutionary Microbiology, 2005, (55), 973-976 and J Ind Microbiol Biotechnol 2009, DOI 10.1007/s10295-009-0638-4. These "methylotrophic" yeasts have found particular utility in the production of recombinant polypeptides. Many yeasts formerly known as *Pichia*, notably the yeast known as *Pichia pastoris*, have been reassigned to the genus *Komagataella*, and yeasts known as *Pichia angusta* and *Hansenula polymorpha* have been reassigned to the genus *Ogataea*. Herein, the naming convention followed by Kurtzman in J Ind Microbiol Biotechnol 2009, DOI 10.1007/s10295-009-0638-4 is followed.

Recombinant gene expression and translation is a complex and not fully understood process. The key factors influencing the productivity of recombinant protein in eukaryotes such as yeasts include the promoter, copy number of the gene of interest, the site of integration (integrant recombinants), plasmid copy number and stability (autonomously replicating plasmid based systems), processing of pre-pro sequences, secretion leader, secretion and folding capacity and the presence 5'-untranslated leader sequences.

One of the distinguishing features of the methylotrophic yeast Pichia pastoris is the inability to assimilate many carbon sources including galactose (N. J. W. Kreger-van Rij, The Yeasts a Taxonomic Study, Edited by J. Lodder, 1970, North-Holland Publishing Company) indicating the absence of, or a non-functional, GAL regulon. In the course of the studies leading to the present invention, even Pichia pastoris strains noted as being "positive" for assimilation of galactose (CBS9173 and CBS9175 (CBS-KNAW Fungal Biodiversity Centre, Utrecht, Netherlands)) were observed not to grow on medium where galactose was the sole carbon source.

The GAL regulon in the yeast *Saccharomyces cerevisiae* has been extensively studied and characterised. The GAL1/GAL10 gene regulatory sequence of *S. cerevisiae* is responsive to both galactose and glucose. The regulatory sequence is involved in the regulation of galactose metabolism in *S. cerevisiae* through the controlled expression of the enzymes responsible for the utilisation of galactose as a carbon source (Lohr, et al., FASEB J. 9:777-787 (1995)). Recent advances have described the evolutionary aspects of the GAL regulon amongst different yeast species (Slot and Rokas, Proc Natl Acad Sci USA. 2010 Jun. 1; 107(22): 10136-10141) which indicate the presence of the GAL regulon in the non-methylotrophic yeast *Pichia stipitis* but not the biotechnologically important yeasts *Pichia pastoris, Komagataella pastoris* or *Hansenula polymorpha*. Galactose is known to be transported into the *S. cerevisiae* yeast cell by a specific permease, that is encoded by the GAL2 gene. The expression of GAL regulon genes in *S. cerevisiae* is tightly and precisely regulated. In the presence of galactose as a carbon source the expression of the GAL regulon genes is activated/enhanced. When cells are grown on glucose as a carbon source the glucose acts as a repressor of the GAL regulon even when galactose is present with glucose. The product of the GAL4 gene (GAL4p protein) plays an important role in the regulation of the GAL regulon genes and is involved in the expression of GAL1, GAL2, GAL7, and GAL10 genes. In the native *S. cerevisiae* GAL regulon GAL1, GAL7, and GAL10 genes code for proteins galactokinase, transferase, and epimerase that are required for galactose metabolism by the yeast. Galactokinase (EC 2.7.1.6) is an enzyme which catalyzes the conversion of the sugar galactose (inducer) into galactose-1-phosphate. In summary, in the native *S. cerevisiae* system in the absence of galactose, GAL80 protein binds to GAL4 protein and prevents it from acting as a transcription-enhancing factor for GAL1, GAL7, and GAL10 genes. When galactose is present, it binds to GAL80 protein, leading it to dissociate from GAL4 protein. The GAL4 protein then binds to the $UAS_G$ (galactose specific upstream activating sequence) associated with each of GAL1, GAL7, and GAL10 genes and activates transcription of GAL1, GAL7 and GAL10 genes.

US2003/040047 discloses the use of a GAL1 promoter to express the CMK2 gene in *Hansenula polymorpha* (now known as *Ogataea polymorpha*). The regulation of the GAL system in biotechnologically important yeast *Komagataella phaffii* (commonly known as *Pichia pastoris* or *Komagataella pastoris*) has not been described. Further the use of the GAL10 promoter for the expression of recombinant proteins in methylotrophic yeasts have not been described.

An understanding of carbon catabolite repression in the yeast *Pichia pastoris* is largely limited to the effects on recombinant systems using the AOX1 promoter system (for example see Inan and Meagher, Journal of Bioscience and Bioengineering, Vol. 92, No. 6, 585-589. 2001). Catabolite repression in the yeast *S. cerevisiae* has been extensively characterized and is better understood (for review see Juana M. Gancedo, Microbiology and Molecular Biology Reviews, June 1998, p. 334-361). Glucose repression in *S. cerevisiae* is mediated by Mig1 (multicopy inhibitor of galactose gene expression), a zinc finger protein (Nehlin and Ronne H, 1990, EMBO J 9(9):2891-8). The Mig1 protein binds to the promoters of many genes and represses their transcription. Repression by Mig1 protein is believed to be both direct and indirect, through repression of genes encoding transcriptional activators. One example of this are the GAL genes, which are repressed both directly by Mig1 protein, and indirectly through repression of the GAL4 gene in *S. cerevisiae*.

According to one aspect of the present invention, there is provided a recombinant yeast of the genus *Komagataella* which has been transformed with a galactose promoter.

According to a further aspect of the present invention, there is provided a process for the production of a recombinant polypeptide which comprises expressing an expression cassette for the recombinant polypeptide in a yeast of the genus *Komagataella* wherein the expression cassette is operably linked to a galactose promoter.

According to another aspect of the present invention, there is provided a method for preparing a yeast strain, which comprises transforming a yeast of the genus *Komagataella* with a vector comprising a galactose promoter.

According to a still further aspect of the present invention, there is provided a vector for expression of a recombinant polypeptide in a yeast of the genus *Komagataella*, comprising a galactose promoter flanked by regions homologous to the *Komagataella* genome, preferably the alcohol oxidase gene, and most preferably the AOX1 gene of *Komagataella phaffii*.

The presence of regions homologous to the *Komagataella* genome enables the vector comprising the galactose promoter to integrate into the *Komagataella* genome. Selection of appropriate homologous regions enables integration into sites known to be effectively transcribed. Alternatively, yeast Autonomously Replicating Sequences or yeast DNA plasmids containing the expression system may also be used.

Yeasts of the genus *Komagataella* which can be employed in these aspects of the present invention include but are not limited to *Komagataella pastoris*, *Komagataella phaffii* and *Komagataella pseudopastoris*. *Komagataella phaffii* is especially preferred. Examples of *Komagataella* strains which can be employed include ATCC 76273, 28485, 201949 and 20864 (American Type Culture Collection, Manassas, Va., USA); NCYC 175 (Type strain, National Collection of Yeast Cultures, Norwich, UK); GS115, KM71 and X33 (Invitrogen Corporation, Carlsbad, Calif., USA); and CBS9173 and CBS9175 (CBS-KNAW Fungal Biodiversity Centre, Utrecht, Netherlands). A preferred strain of *Komagataella pastoris* is the strain available from the Agriculture Research Service designated NRRL Y-1603, or from the Centraalbureau voor Schimmelcultures designated CBS704. A preferred strain of *Komagataella phaffii* is the strain available from the Agriculture Research Service designated NRRL Y-7556 or from the Centraalbureau voor Schimmelcultures designated CBS2612. A preferred strain of *Komagataella pseudopastoris* is the strain available from the Agriculture Research Service designated NRRL Y-27603, or from the *Centraalbureau voor Schimmelcultures* designated CBS9187. In many embodiments of the present invention, the most preferred yeast is the *Komagataella phaffii* strain available from the Agriculture Research Service designated NRRL Y-11430, or from the Centraalbureau voor Schimmelcultures designated CBS7435.

Galactose promoters which can be employed in the present invention include promoters from the *Saccharomyces cerevisiae* GAL regulon, and especially the GAL1 or GAL10 promoters. Preferably a combination of GAL1 and GAL 10 is employed as promoter. In certain embodiments, the GAL1 and GAL10 promoters are orientated in different transcriptional directions. When both GAL1 and GAL 10 promoters are employed, either, and especially GAL10, can be operably linked to a single expression cassette for a polypeptide. In some embodiments, the GAL1 and GAL10 promoters can be operably linked to expression cassettes for different polypeptides, such as the heavy and light chains of an antibody fragment. In other embodiments, the GAL1 and GAL10 promoters can be operably linked to expression cassettes for the same protein. In such embodiments, the genes encoding the protein employed are most preferably different genes in order to avoid potential instability.

In certain highly preferred embodiments, the galactose promoter, and preferably both GAL1 and GAL10 promoters, is employed in combination with a *Saccharomyces cerevisiae* GAL4 operon.

In related embodiments, there is provided a vector for expression of a recombinant polypeptide in a methylotrophic yeast strain comprising a GAL10 promoter, preferably flanked by regions homologous to the methylotrophic yeast genome, preferably the alcohol oxidase gene, and most preferably the AOX1 gene of *Komagataella phaffii*, or alternatively the vector comprises a yeast Autonomously Replicating Sequence or yeast DNA plasmid, a recombinant methylotrophic yeast which has been transformed with a GAL10 promoter, a process for the production of a recombinant polypeptide which comprises expressing an expression cassette for the recombinant polypeptide in a methylotrophic yeast wherein the expression cassette is operably linked to a GAL10 promoter and a method for preparing a yeast strain, which comprises transforming a methylotrophic yeast with a vector comprising a GAL10 promoter.

Methylotrophic yeasts which can be employed in these related embodiments of the invention include but are not limited to yeasts capable of growth on methanol, and especially members of the genuses *Komagataella* and *Ogataea*. Preferred yeasts include *Komagataella pastoris*, *Komagataella phaffii*, *Komagataella pseudopastoris* and *Ogataea polymorpha* (also known as *Pichia angusta*). *Komagataella phaffii* is especially preferred. Examples of yeasts that can be employed include those of the genus *Komagataella* listed above in respect of the first aspect of the present invention.

Vectors employed in the present invention preferably comprise at least one selectable marker, for example an antibiotic resistance marker such as kanamycin or Zeocin resistance, or an auxotrophic marker, for example a gene conferring an ability to synthesise an amino acid which the untransformed host strain could not. Examples of selectable markers are well known in the art.

In certain embodiments of the present invention, the vectors and host strains comprise an operator sequence such as lac, gal, deo or gin. In many instances, 1, 2 or 3 operators are present. In some embodiments, an operator sequence overlaps with the transcriptional start point. Preferably, the operator sequence(s) are perfect palindrome sequences, especially the sequence GGAATTGTGAGCGCTCACAATTCC (nucleotides 646 to 669 of SEQ ID NO: 1). When two or more operators are present, two of the operators are preferably spaced from 85 to 150 base pairs apart, preferably from 90 to 126 base pairs apart, and most preferably 91 or 92 base pairs apart. Operator sequences may be located upstream or downstream of the galactose promoter operably liked to the expression cassette for a polypeptide, and in certain instances, at least one operator may be located upstream and at least one operator may be located downstream of the galactose promoter operably linked to the expression cassette for a polypeptide. When GAL1 and GAL10 promoters are employed oriented in different transcriptional directions and each is operably linked to an expression cassette for a polypeptide, an operator sequence may be located downstream of each promoter.

It will be recognised that the operator system is commonly employed with an appropriate repressor sequence. Repressor sequences produce repressor protein, for example lacI gene sequence when using the lac operators. Other lac repressor sequences may also be used, for example the lacI$^Q$ sequence can be used to increase the level of lac repressor protein. The repressor sequence may also be provided by the host cell genome or by using an additional compatible plasmid.

In some embodiments, the vectors of the present invention comprise an expression cassette for a repressor protein additional to, or as an alternative to, that associated with any operator sequence that may be present. One preferred example is a cassette expressing *Saccharomyces cerevisiae* Mig1 protein. In the presence of a feed comprising a carbon source, such as glucose, which mediates expression of the Mig1 protein, the Mig1 protein serves to inhibit expression of the GAL1 promoter controlled expression cassettes. Adjusting the feed to replace the Mig1 mediating carbon-source with, or to provide a preponderance of, a carbon source which represses Mig1 expression reduces the inhibition of the GAL1 promoter controlled expression cassettes. The presence of such an expression cassette for a repressor protein such as Mig1 therefore provides the option of controlling the expression of the target recombinant polypeptide. In certain embodiments, where a GAL4 operon is employed, mediation or repression of the expression of Mig1 protein can be employed to modulate the effect of expression of the GAL4 operon.

The vectors employed in the present invention may also comprise one or more of insertable nucleic acid sequences, being nucleic acid sequences homologous to the host genomic DNA. Such sequences are selected to achieve integration of vectors at desired locations of the host genome, and examples are well known in the art, including alcohol oxidase gene sequences, dihydroxyacetone synthase gene sequences, p40 gene sequences and HIS4 gene sequences.

The vectors of the present invention may also comprise one or more of insertion sites, such as a polylinker site, to facilitate the insertion of, for example, structural genes or cassettes; a termination sequence, especially a 3'-termination sequence, and bacterial plasmid DNA and/or bacteriophage DNA to enable the amplification and maintenance of these vectors in bacterial hosts.

The vectors of the present invention are assembled by methods known in the art, for example gene synthesis of the desired nucleotide sequence, and/or by ligation of components into vectors comprising appropriate insertion sites.

Methylotrophic yeast are transformed with vectors according to the present invention by methods known in the art, such as chemical transformation, electroporation and sphaeroplast fusion.

Strains transformed with vectors according to the present invention are commonly selected by methods appropriate to any selection marker present on the vector, for example culturing in the absence of a given nutrient for an auxotrophic host strain where the selectable marker enables synthesis of the absent nutrient, or by culturing in the presence of a given antibiotic where an antibiotic-resistance marker is employed.

The expression system is expressed by methods well known in the art for the cells employed. Preferred expression methods include culturing the recombinant cells in growth medium, especially by fermentation, and then recovering the expressed protein. The term "growth medium" refers to a nutrient medium used for growing the recombinant cells. In many embodiments, a nutrient solution is employed. Suitable growth media for given recombinant cells are well known in the art. In certain embodiments of the present invention, the growth medium comprises a sugar selected from the group consisting of glucose, galactose, sucrose and sorbitol. Additional carbon sources, such as methanol, may be employed if desired.

It will be recognised that the conditions, especially feed and growth conditions, for the expression of the vector according to the present invention, and depending for instance on the nature of the recombinant polypeptide, can be varied to achieve the desired performance criteria. For example, in some instances, higher overall yields of polypeptide can be achieved by favouring expression of the recombinant polypeptide throughout the culturing of host cells. In other instances, higher yields may be achieved by repressing expression of the recombinant polypeptide until a desired cell density is achieved, and then de-repressing and or inducing expression, such as by adjusting the carbon source, and/or adding an inducer, such as IPTG, appropriate to the nature of operator sequences. In certain preferred embodiments of the present invention, repression is achieved by maintaining a feed solution comprising glucose as the dominant or sole carbon source, and then when desired, replacing the glucose with an alternative carbon source such as sucrose, sorbitol or preferably galactose, or a combination thereof, and/or adding an inducer.

The invention is illustrated without limitation by the following examples.

COMPARATIVE EXAMPLE 1

Growth of *Komagataella* Yeast Strains on Galactose

The growth of strains ATCC 76273, 28485, 201949 and 20864 (American Type Culture Collection, Manassas, Va., USA); NCYC 175 (Type strain, National Collection of Yeast Cultures, Norwich, UK); GS115, KM71 and X33 (Invitrogen Corporation, Carlsbad, Calif., USA), each commonly known as Pichia pastoris or *Komagataella pastoris*, was examined by streak plating in duplicate onto minimal agar plates (phosphate buffer, yeast nitrogen base, biotin, histidine and either glucose or galactose as the primary carbon source) as is well established in the art. The plates were incubated at 25-30° C. for 72 hours. Growth was recorded and the cultures re-streak plated a further two times sequentially onto fresh media as described above to ensure growth was related to the carbon source provided and not due to carry over of nutrients from the starting stock culture. None of the strains grew on minimal medium containing galactose as the sole carbon source. Confluent growth was observed with all strains on minimal medium containing glucose.

To further confirm the absence of metabolism of galactose by the *Komagataella* strains they were tested for the ability to assimilate galactose by using the API50CH (bioMerieux SA, Marcy I'Etoile, France) test strips (as is well established in the art). All 8 *Komagataella* hosts strains tested negative for galactose metabolism.

The results obtained indicated that none of the *Komagataella* host strains tested were able to metabolise or grow on galactose as the sole carbon source whereas, as expected, all the host strains grew well on media containing glucose as the primary carbon source (control).

COMPARATIVE EXAMPLE 2

Growth of Gal-Positive *Pichia* Yeast Strains on Galactose on Plates

*Komagataella* (*Pichia*) *pastoris* strains CBS9173 and CBS9175 (CBS-KNAW Fungal Biodiversity Centre, Utrecht, Netherlands) are described in the on-line CBS-KNAW Fungal Biodiversity Centre database (www.cbc.knaw.nl, accessed 27 May, 2011) as positive ('w', weak CBS9173, '+' positive CBS9175) for assimilation of galactose as a carbon source. Both host strains were tested for the ability to grow on galactose as the sole carbon source as described in Example 1.

Both CBS9173 and CBS 9175 strains showed no significant growth on media containing galactose with no significant difference between CBS9173 (noted as 'weak' growth in the CBS-KNAW database) and CBS9175 (noted as 'positive' growth in the CBS-KNAW database).

Surprisingly, given the data in the CBS-KNAW database no growth on minimal medium with galactose as the sole carbon source was observed for both strains with no difference between them compared to growth of both strains in the same medium with glucose as the sole carbon source.

COMPARATIVE EXAMPLE 3

Growth of Gal-Positive *Komagataella* Yeast Strains in Galactose in Liquid

The growth of strains CBS9173 and CBS 9175 in liquid was examined. A 1 ml frozen stock culture of each strain was thawed and used to inoculate 600 ml of YNB+Gly broth (1.5 g/L yeast nitrogen base, 12 g/L potassium di-hydrogen phosphate, 2.7 g/L di-potassium hydrogen phosphate, 32 g/L glycerol), pH 5.0 in a 3 L Erlenmeyer baffled flask. The flasks were incubated at 28-30° C., 250 rpm for 48 hours. The cells were harvested and washed in sterile ¼ Ringers solution and used to inoculate 50 ml of fresh YNB+Gly broth and YNB supplemented with 1% galactose (YNB+Gal) in a 250 ml baffled Erlenmeyer flask. The flasks were incubated as described above. Samples were taken at regular intervals to determine growth (optical density $OD_{600}$). The results showed that neither CBS9173 or CBS9175 grew in growth medium with galactose as the sole carbon source. An aliquot of each culture from the YNB+Gal flasks from the end of the incubation (336 h) was transferred to fresh YNB+Gly medium (50 ml in 250 ml flasks) and incubated under the conditions described above for 5 days. Both strains grew well ($OD_{500}$=13-17) confirming that the strains when incubated in galactose containing medium did not proliferate but maintained cell viability such that when the strains are transferred to a medium containing a utilisable carbon source growth was restored/observed.

Taken together the results described in Comparative Examples 1-3 clearly demonstrate the surprising observation that the *Komagataeila pastoris* strains do not metabolise galactose and thus do not grow in growth medium where galactose is the sole carbon source.

EXAMPLE 4

Vector Construction

A vector was constructed in which the gene for human serum albumin (h-SA, (SEQ ID No. 4) with the mating factor α secretion leader sequence (MFα)) as cloned downstream of a modified GAL1/GAL10 (GAL1/mGAL10) promoter (SEQ ID No. 1). The GAL1/GAL10 promoter was modified (GAL1/mGAL10) to include a perfect palindromic Lac operator sequence (at positions 648 to 667 of SEQ ID NO. 1). In the absence of the LacI repressor gene and thus LacI repressor protein in a cell no binding of the LacI repressor protein can occur at the perfect palindromic Lac operator site. SEQ ID No. 1, which contains the GAL1/mGAL10 promoter sequence was digested with EcoRI and NotI, and the h-SA fragment ((SEQ ID No. 2), which had also been digested with EcoRI and NotI was cloned downstream of the mGAL10 promoter (0142-1-2). This fragment was then ligated to a vector containing a Zeocin resistance marker and the *Pichia pastoris* 5' AOX region (SEQ ID No. 3). SEQ ID No. 3 was digested with NotI and BamHI, and 0142-1-2 digested with BglII and NotI. The two fragments were ligated together and then transformed onto *E. coli* strain XL1-Blue-MR (Stratagene). Recombinant plasmids were screened by restriction digest as is well established in the art and authenticity confirmed by DNA sequencing. The resultant plasmid expressing h-SA using the GAL1/mGAL10 system was named pAVE297.

The gene for human serum albumin (h-SA with the native h-SA leader (SEQ ID No. 6) was cloned as NdeI/XmnI/PsiI fragment into a NdeI/XmnI fragment of pAVE297. Note SEQ ID No.6 is 'cut' with PsiI as gene sequence has two XmnI sites and PsiI 'cuts' the unwanted fragment in half. Recombinant plasmids were screened by restriction digest and authenticity confirmed by DNA sequencing. The resulting plasmid was named pAVE326. The vector pAVE326 is designed to express/secrete h-SA using the GAL1/mGAL10 system when integrated into the genome of the yeast *Komagataella*.

The *E. coli* LacI gene was cloned as is well established in the art as a BglIII/EcoRI fragment into MfeI/BglIII digested plasmid pAVE297. Recombinant plasmids were screened by restriction digest and authenticity determined by DNA sequencing. The resultant plasmid was named pAVE304. Surprisingly DNA sequencing indicated that the LacI gene sequence in pAVE304 had become truncated during cloning and was thus the LacI repressor protein produced by the truncated gene was probably non-functional. The lacI gene was re-designed and a synthetic *E. coli* LacI gene (SEQ ID NO. 5) was then cloned as BtsI/SspI fragment into a BtsI/SspI fragment of pAVE304.

Recombinant plasmids were screened by restriction digest and authenticity confirmed by DNA sequencing. The resulting plasmid was named pAVE506. The vector pAVE506 is designed to express/secrete h-SA using the GAL1/mGAL10 system, with expression repression control provided by the perfect palindromic Lac operator sequence within the GAL10 promoter (mGAL10) and binding of the LacI repressor protein to the perfect palindromic lac operator site, when integrated into the genome of the yeast *Komagataella*.

A synthetic GAL4 gene was designed (SEQ ID No. 7) together with the GAL4 native promoter and was cloned as a BglIII/NotI fragment into a BglIII/NotI fragment of vector pTEF-Bsd (Invitrogen Corporation, Carlsbad, Calif., USA). Vector pTEF1/Bsd contains a blasticidin resistance gene expressed from either the EM7 bacterial promoter or the *S. cerevisiae* TEF1 promoter immediately upstream of a CYC1 transcription termination sequence. The vector also includes a pUC origin of replication and ampicillin resistance gene for propagation in *E. coli*. Recombinants plasmids were screened by restriction digest and authenticity confirmed by DNA sequencing. The gene for resistance/selection using the antibiotic kanamycin (SEQ ID NO. 8) was cloned as a NcoI/Eco53KI fragment into a NcoI/StuI fragment of this plasmid. Recombinant plasmids were screened by restriction digest and authenticity confirmed by DNA sequencing. The resulting plasmid was named pAVE345, having the sequence given in SEQ ID No. 9. The vector pAVE345 is designed to constitutively express the GAL4 'activator' protein when integrated into the genome of the yeast *Komagataella*.

The starting vector for the generation of pAVE355 was vector pTEF1/Bsd (Invitrogen Corporation, Carlsbad, Calif., USA). Vector pTEF1/Bsd contains a blasticidin resistance gene expressed from either the EM7 bacterial promoter or the *S. cerevisiae* TEF1 promoter immediately upstream of a CYC1 transcription termination sequence. The vector also includes a pUC origin of replication and ampicillin resistance gene for propagation in *E. coli*. The blasticidin resistance gene was replaced with a synthetic kanamycin resistance gene, cloned as an NheI/EcoRI fragment. The DNA sequence is provided (SEQ ID No. 10). Ligation mixtures were transformed into *E. coli* cloning host strain XL-1 Blue MR (Stratagene). Initial screening of transformants was by restriction digestion using NheI/EcoRI. The authenticity of the sequence was confirmed by DNA sequencing. The resultant plasmid was named pAVE355. A synthetic *S. cerevisiae* Mig1 gene under the control of the *Komagataella* GAP promoter (SEQ ID No. 11) was cloned into vector pAVE355 as a BamHI/HindIII fragment to generate vector pAVE359. Vector pAVE359 is designed to constitutively express the Mig1 protein when integrated into the *Komagataella* genome.

EXAMPLE 5

Transformation of Yeast Host Strains

The following method was used to generate recombinant *Komagataella* clones with the appropriate expression vector cassette integrated into the genome. As is well established in the art expression vector integrations into the *Komagataella* host genome produce clones which demonstrate differences in expression level primarily (but not always) related to the copy number of the expression cassette at the site of integration into the genome. Clones are then screened for productivity of the target/desired gene of interest. Non-recombinant *Komagataella* host strains were inoculated into 50 ml volume of sterile YPD broth (10 g/L yeast extract, 20 g/L peptone, 20 g/L dextrose) in a 250 ml conical flask and the flasks incubated at 30° C. with shaking (220 rpm) in an orbital shaking incubator for 16-17 hours or until growth (determined by measuring culture optical density) reached $OD_{600\,nm}$ of 1.3 to 1.5. This culture (0.1-0.5 ml) was then used to inoculate 500 ml volume of fresh YPD broth in a 2 L conical flask and incubated as described above. The cells were harvested and centrifuged at 1500×g for 5 minutes at +4° C. The cell pellet was re-suspend in 500 ml of ice-cold (0° C.), sterile water and re-centrifuged as described above and the cell pellet re-suspended again in 250 ml of ice-cold (0° C.), sterile water. This cell suspension was re-centrifuged as described above and the cell pellet re-suspended in 20 ml of ice-cold (0° C.) 1M sorbitol solution. The cell suspension in sorbitol solution was re-centrifuged as described above and the cell pellet re-suspend in 1 ml of ice-cold (0° C.).

1M sorbitol solution, 80 μl of the cell suspension was mixed with 20-40 μg of linearised vector DNA (in 5-10 μl sterile water) and transferred them to a pre-chilled (ice-cold (0° C.)) 0.2 cm electroporation cuvette and the cuvette incubated on ice for 5 minutes.

Transformation of the DNA was carried out by electroporating the cells as is well established in the art (1500V charging voltage, 25 μF capacitance, 200Ω resistance). Immediately after electroporation, 1 ml of ice-cold 1M sorbitol solution was added to the electroporation cuvette and the contents of the cuvette transferred to a sterile 15 ml sample tube and incubated at 30° C. (static) for 1-2 hours. Following incubation the post electroporation mixture was plated onto YPD agar plates supplemented with sorbitol and the appropriate concentrations of the selection antibiotic (based on the selection marker included in the expression vector) as is well established in the art. The plates were incubated for 3-10 days at 30° C. until colonies had formed. Individual colonies were re-streaked onto YPD agar supplemented with sorbitol/selection antibiotic to establish monoclonality and re-confirm resistance to the selection antibiotic. Transformant integrant clones were further expanded to produce glycerol stock cyrovials (1 ml, stored at −70° C.) as is well established in the art. The description of the strains constructed are provided in Table 1. The performance of the clones is described in the examples provided below where the recombinant strain designation, e.g. CLDxxx denotes the combination of host strain and expression vector, e.g. pAVEyyy. Where a second expression cassette was transformed (e.g. with pAVEyyy) into a recombinant strain (e.g. CLDxxx) the new strain generated is denoted CLDxxxpAVEyyy. Individual clones from transformations are described by the denomination CLDxxx-01, -02, -03, -04, etc.

TABLE 1

Recombinant Strains

| Final Recombinant Strain Designation | Host Strain/ Starting strain | Integrating Vector used for Transformation | Target Protein Expressed | System Summary |
|---|---|---|---|---|
| CLD390 | ATCC20864 | pAVE326 | h-SA | GAL1/mGAL10 |
| CLD391 | CBS9175 | pAVE326 | h-SA | GAL1/mGAL10 |
| CLD446 | NRRL11430* | pAVE326 | h-SA | GAL1/mGAL10 |
| CLD446pAVE345 | CLD446 | pAVE345 | h-SA | GAL1/mGAL10 plus GAL4 |
| NRRL11430pAVE506 | NRRL11430* | pAVE506 | h-SA | GAL1/mGAL10 plus LacI |
| NRRL11430pAVE678 | NRRL11430 | pAVE678 | h-SA | GAL1/mGAL10 plus *Komagataella* Mig1 |
| NRRL11430pAVE359 | NRRL11430 | pAVE359 | h-SA | GAL1/mGAL10 plus *S. cerevisiae* Mig1 |
| CLD446pAVE359 | CLD446 | pAVE359 | h-SA | GAL1/mGAL10 plus *S. cerevisiae* Mig1 |

*NRRL 11430 = *Komagataella phaffii* (Northern Regional Research Laboratories, National Center for Agricultural Utlization Research, Peoria, Illinois, USA)

EXAMPLE 6

Frozen glycerol stocks of clones of CLD390 and CLD391 were thawed and individually inoculated into 50 ml YP broth (10 g/L yeast extract, 20 g/L peptone) supplemented with 20 g/L glucose. Growth and h-SA secretion was determined by periodically sampling the flasks and determining growth ($OD_{600}$) and h-SA secretion (ELISA) as is well established in the art. Flasks were incubated for 120 hours under the conditions described. The h-SA volumetric titre is presented in Table 2.

TABLE 2

Volumetric h-SA titre

| Strain | Titre (120 hours) ng/ml (ELISA) |
|---|---|
| CLD390 | 8.1 |
| CLD391 | 22.0 |

Surprisingly, constitutive expression and secretion of h-SA (using the native h-SA secretion leader) was demonstrated using the GAL1/mGAL10 promoter system. This is the first demonstration of the GAL1/mGAL10 system in the yeast *Komagataella* for the expression of recombinant proteins and was totally un-expected given that growth studies (described in Examples 1-3) had clearly indicated that *Komagataella* strains did not metabolise or assimilate galactose and thus one of ordinary skill in the art would assume that *Komagataella* strains did not possess the functional elements/auxiliary factors required to support activity of the GAL1/mGAL10 system. Equally surprising was that expression and secretion recombinant protein was observed in the presence of glucose which in *S. cerevisiae* is well known in the art to repress the GAL regulon.

EXAMPLE 7

Frozen glycerol stocks of clones of CLD390 and CLD391 were thawed and individually inoculated into 50 ml YP broth (10 g/L yeast extract, 20 g/L peptone) supplemented with various additional carbon sources to determine the effect of the additional carbon sources on growth and h-SA secretion level when using YP broth. The flask were incubated at 30° C., 220 rpm in an orbital shaker. The concentration of the additional carbon sources was 20 g/L galactose, 20 g/L sucrose, and 20 g/L sorbitol. Growth and h-SA secretion was determined by periodically sampling the flasks and determining growth ($OD_{600}$) and h-SA secretion (ELISA) as is well established in the art. Flasks were incubated for 120 hours under the conditions described. The h-SA volumetric titre (ng/ml) was to the specific productivity achieved in YP+Glucose medium (Example 6, YP+Glucose=1.0) are presented in Table 3.

TABLE 3

| Strain | Relative Specific Productivity carbon source | | | |
|---|---|---|---|---|
| | Glu | Gal | Suc | Sor |
| CLD390 | 1 | 17 | 17 | 27 |
| CLD391 | 1 | 7 | 8 | 7 |

The results obtained demonstrated a dramatic and un-expected increase (relative to that achieved with glucose (Example 6)) in the expression and secretion of h-SA when the growth medium was supplemented with galactose, sucrose or sorbitol. Relative to the productivity achieved with growth medium supplemented with glucose the productivity increased 17-27x with CLD390 (host ATCC20864) and ca. 7x with CLD391 (host CBS9175). The increase in specific productivity in the presence of galactose was surprising given the results described in Example 1-3 which clearly demonstrated that the host cells did not grow on or metabolise galactose as the sole carbon source. The skilled person will appreciate how the GAL1/mGAL10 promoter system can be exploited for the production of recombinant proteins using the yeast *Komagataella* as a host and also how the surprising influence of carbon sources such as galactose, sucrose and sorbitol can be used to increase and optimise productivity yet further.

EXAMPLE 8

Frozen glycerol stock of CLD391 was thawed and individually inoculated in duplicate (Flask 1 and Flask 2) 50 ml YP broth (10 g/L yeast extract, 20 g/L peptone) supplemented with various additional carbon sources to confirm the effect of the glucose, galactose and sorbitol carbon sources on growth and h-SA secretion level observed in Example 7. The flasks were incubated at 30° C., 220 rpm in an orbital shaker. The concentration of the additional carbon sources was 20 g/L glucose, 20 g/L galactose, and 20 g/L sorbitol. Growth and h-SA secretion was determined by periodically sampling the flasks and determining growth ($OD_{600}$) and h-SA secretion (ELISA) as is well established in the art. Flasks were incubated for 120 hours under the conditions described. The h-SA volumetric titre (ng/ml) was converted to a specific productivity (ng/ml/$OD_{600}$). The results expressed relative to the specific productivity achieved in YP+Glucose medium are presented in Table 4

TABLE 4

| Flask | Relative Specific Productivity carbon source | |
|---|---|---|
| | Gal | Sor |
| 1 | 15 | 26 |
| 2 | 11 | 42 |

The data obtained confirmed the surprising results described in Example 7. Expression and secretion when CLD391 was grown in YP medium supplemented with glucose was confirmed with significant increases (11-42 fold) in constitutive expression of recombinant protein and secretion using the GAL1/mGAL10 expression system with galactose or sorbitol supplements to the growth medium.

EXAMPLE 9

Frozen glycerol stock of CLD391 was thawed and used to inoculate 50 ml of YP broth (10 g/L yeast extract, 20 g/L peptone) and incubated at 30° C., 220 rpm in an orbital shaker. The cells were harvested, washed using sterile phosphate buffered saline solution and a cell re-suspension used to individually inoculate duplicate flasks (Flask 1 and Flask 2) containing 50 ml YP broth alone and duplicate flasks supplemented with 20 g/L glucose to determine the effect glucose on growth and h-SA expression and secretion level. The flasks were incubated at 30° C., 220 rpm in an orbital shaker. Growth and h-SA secretion was determined by periodically sampling the flasks and determining growth ($OD_{600}$) and h-SA secretion (ELISA) as is well established in the art. Flasks were incubated for 120 hours under the conditions described. The h-SA volumetric titre (ng/ml) was converted to a specific productivity (ng/ml/$OD_{600}$). The results expressed relative to the specific productivity achieved in YP+Glucose medium are presented in Table 5.

TABLE 5

| Flask | Relative Specific Productivity carbon source | |
|---|---|---|
| | Glu | None |
| 1 | 1 | 3 |
| 2 | 1 | 3.6 |

The results obtained indicate that the GAL1/mGAL10 system in *Komagataella* expresses protein constitutively (YP medium) with glucose supplements to the growth medium having a 'repressive' effect on protein expression and secretion. Thus one skilled in the art will understand how glucose supplements to the growth medium (basal media, added as bolus feeds or continuous feeds) can be used to optimize recombinant protein production using the GAL1/mGAL system in *Komagataella*.

EXAMPLE 10

Frozen glycerol stock of CLD391 was thawed and individually inoculated into 50 ml YP broth (10 g/L yeast extract, 20 g/L peptone) supplemented with various additional carbon sources to confirm the effect of the additional carbon sources on growth and h-SA secretion level. The flasks were incubated at 30° C., 220 rpm in an orbital shaker. The concentration of the additional carbon sources was 20 g/L glucose, 20 g/L glycerol, 20 g/L and galactose. The influence of carbon source combinations was examined using YP broth supplemented with 20 g/L galactose plus 20 g/L glucose and 20 g/L galactose plus 20 g/L glycerol. Growth and h-SA secretion was determined by periodically sampling the flasks and determining growth ($OD_{600}$) and h-SA secretion (ELISA) as is well established in the art. Flasks were incubated for 120 hours under the conditions described. The h-SA volumetric titre (ng/ml) was converted to a specific productivity (ng/ml/$OD_{600}$). The results expressed relative to the specific productivity achieved in YP+Glucose medium are presented in Table 6

TABLE 6

| Relative Specific Productivity | | | | |
|---|---|---|---|---|
| YP + Glu | YP + Gly | YP + Gal | YP + Gal + Glu | YP + Gal + Gly |
| 1 | 0.4 | 7.4 | 0.5 | 0.3 |

The results obtained showed constitutive expression was achieved with YP broth supplemented with glucose or glycerol as additional carbon sources. YP broth supplemented with galactose demonstrated 'induction/enhancement' of recombinant protein expression when compared to both YP broth supplemented with glucose or glycerol. Both glucose and glycerol when added to YP broth containing galactose abolished the 'induction/enhancement' of recombinant protein expression. The results presented in Examples 7, 8, 9 and 10 to the skilled artisan would indicate (i) how glucose and/or glycerol supplements (to the basal growth media, added as bolus additions or fed into the culture) can be used to 'repress' Komagataella recombinants expressing protein, or (ii) how other carbon sources such as galactose, sucrose and sorbitol can be added (to basal growth media, added as bolus additions or fed into the culture) can be used to enhance/stimulate expression using the GAL1/mGAL10 expression system. It will also be apparent to the skilled artisan how combinations of carbon sources that 'repress' or 'induce/enhance' expression could be used to fine tune expression and thus optimize production of recombinant proteins from the GAL1/mGAL10 system in Komagataella.

EXAMPLE 11

CLD446pAVE345 clones isolated from a transformation of CLD446 with the vector pAVE345 were individually inoculated into 3 ml of YP broth supplemented with 2% w/v glucose and 100 µg/ml G418 in sterile conical tubes. The cultures were incubated at 28° C. for 16±2 hours with shaking at 220 rpm. 50 µl of each culture was then used to inoculate separately 2 ml YP broth with 2% w/v glucose (YPglu) in deep well microtitre plates. A sub-set of the clones were also grown in YP broth supplemented with 2% w/v galactose (YPgal). The plates were sealed to prevent cross contamination between wells whilst permitting gas exchange (air) to facilitate growth. The plates were incubated at 28° C. for 16±2 hours with shaking at 450 rpm for total of 5 days. Samples were withdrawn periodically to determine growth ($OD_{600}$) and titre (ELISA). CLD446 grown in YP=2% w/v glucose (YPglu) achieved a h-SA titre of 64 ng/ml (normalized to 7 ng/ml/OD) after 5 days incubation. The results (120 hours incubation) obtained for the CLD446pAVE345 clones (GAL1/GAL10 plus GAL4) relative to CLD446 are presented in Table 7 (YPglu) and. Table 8 (YPgal)

TABLE 7

| Clone | Relative Specific Productivity |
|---|---|
| CLD446 + pAVE345-01 | 2 |
| CLD446 + pAVE345-02 | 7 |
| CLD446 + pAVE345-03 | 18 |
| CLD446 + pAVE345-04 | 38 |
| CLD446 + pAVE345-05 | 15 |
| CLD446 + pAVE345-06 | 10 |
| CLD446 + pAVE345-07 | 48 |
| CLD446 + pAVE345-08 | 48 |
| CLD446 + pAVE345-09 | 10 |
| CLD446 | 1 |

TABLE 8

| | Relative Specific Productivity medium | |
|---|---|---|
| Clone | YP + Glu | YP + Gal |
| CLD446 + pAVE345-01 | 1 | 85 |
| CLD446 + pAVE345-02 | 6 | 122 |
| CLD446 + pAVE345-03 | 18 | 64 |
| CLD446 + pAVE345-04 | 38 | 1 |
| CLD446 + pAVE345-05 | 14 | 20 |

The results presented in Table 7 clearly exemplify a significant increase in the specific productivity of h-SA secreted using the GAL1/mGAL10 system in Komagataella when the GAL4 protein is co-expressed in the cell—up to ca. 50 fold increase in the relative productivity when compared to the strain without GAL4 co-expression. This was totally un-expected. Surprisingly, GAL4 co-expression with the GAL1/mGAL10 system when the clones are grown in YP broth supplemented with galactose demonstrate a further increase in the relative productivity (versus YPglu medium)—for the majority of the clones evaluated (Table 8). Relative to CLD446 (GAL1/mGAL10, without GAL4) grown in YPglu, clones grown in YPgal achieved increases in specific productivity of h-SA expressed/secreted up to >120 fold. The skilled artisan will understand how recombinant protein titres can be further optimized by optimizing the combination of Komagataella host strain and growth medium supplement, (e.g. glucose, galactose, sucrose, glycerol, sorbitol), in combination with the GAL1/mGAL10/GAL4 system as exemplified in Example 10 previously.

EXAMPLE 12

Komagataella host strain NRRL11430 was transformed with vector pAVE506 as described previously. Individual integrant clones (colonies on selective agar plates) post transformation were expanded in YP medium supplemented with 2% w/v glucose in microtitre plates (28° C.) for 120 hours and screened for h-SA titre using ELISA as is well established in the art. Transformants with a range of productivities were obtained with constitutive titres of up to 1065 ng/ml/OD600 nm.

EXAMPLE 13

Representative NRRL11430pAVE506 clones isolated from a transformation of host NRRL11430 with the vector pAVE506 (Example 12) were individually inoculated into 3 ml of YP broth supplemented with 2% w/v glucose in sterile conical tubes. The cultures were incubated at 28° C. for 16±2 hours with shaking at 220 rpm. 50 µl of each culture was then used to inoculate separately 2 ml YP broth with 2% w/v glucose (YPglu) in deep well microtitre plates. A duplicate set clones were also grown in YP broth supplemented with 2% w/v glucose with 5 mM (final concentration) isopropyl-β-D-thiogalactopyranoside (IPTG) added as a bolus addition at 24 hours intervals. The plates were sealed to prevent cross contamination between wells whilst permitting gas exchange (air) to facilitate growth. The plates were incubated at 28° C. for 16±2 hours with shaking at 450 rpm for total of 5 days. Samples were withdrawn periodically to determine growth ($OD_{600}$) and titre (ELISA). The data (120 hours incubation) for a representative set of clones are presented in Table 10 (no IPTG) and Table 11 (+IPTG). Fold induction in presence of IPTG ((specific productivity of NRRL11430pAVE506 clones in the presence of IPTG relative to NRRL11430pAVE326 (no IPTG)) minus (specific productivity of NRRL11430pAVE506 clones relative to NRRL11430pAVE326 (no IPTG)) is presented in Table 3.

TABLE 10

| Clone | Relative Specific Productivity |
| --- | --- |
| NRRL11430pAVE506-01 | 42 |
| NRRL11430pAVE506-02 | 2 |
| NRRL11430pAVE506-03 | 35 |
| NRRL11430pAVE506-04 | 25 |
| NRRL11430pAVE506-05 | 2 |
| NRRL11430pAVE506-06 | 110 |
| NRRL11430pAVE506-07 | 159 |
| NRRL11430pAVE506-08 | 140 |
| NRRL11430pAVE506-09 | 70 |
| NRRL11430pAVE506-10 | 0 |
| NRRL11430pAVE326 | 1 |

TABLE 11

| Clone | Relative Specific Productivity |
| --- | --- |
| NRRL11430pAVE506-01 | 50 |
| NRRL11430pAVE506-02 | 38 |
| NRRL11430pAVE506-03 | 37 |
| NRRL11430pAVE506-04 | 34 |
| NRRL11430pAVE506-05 | 7 |
| NRRL11430pAVE506-06 | 48 |
| NRRL11430pAVE506-07 | 40 |
| NRRL11430pAVE506-08 | 40 |
| NRRL11430pAVE506-09 | 102 |
| NRRL11430pAVE506-10 | 42 |
| NRRL11430pAVE326 (-IPTG) | 1 |

TABLE 12

Relative fold induction in presence of IPTG

| Clone | Fold induction in presence of IPTG |
| --- | --- |
| NRRL11430pAVE505-01 | 1.2 |
| NRRL11430pAVE505-02 | 23.8 |
| NRRL11430pAVE505-03 | 1.2 |
| NRRL11430pAVE505-04 | 1.3 |
| NRRL11430pAVE505-05 | 6.7 |
| NRRL11430pAVE505-06 | 0.4 |
| NRRL11430pAVE505-07 | 0.3 |
| NRRL11430pAVE505-08 | 0.3 |
| NRRL11430pAVE505-09 | 1.5 |
| NRRL11430pAVE505-10 | >>1000* |

*No h-SA detected when grown in YPglu medium indicating very tight control of basal expression by LacI, depression/induction when clone grown in YPglu bolus fed with 5 mM IPTG at 24 hour intervals.

The data presented in Table 10 clearly indicates that expression/secretion of recombinant protein using the GAL1/mGAL10 system in *Komagataella*, as exemplified by CLD446, when coupled with expression control using the Lac operator/lac repressor system (pAVE506) results in a surprising and significant increase in productivity (ca. 160 fold). This was totally un-expected. Those skilled in the art will appreciate that LacO/LacI control systems are generally employed to reduce basal (constitutive) expression with the inducer, IPTG, then being added to induce protein expression, e.g. clone NRRL11430pAVE506-10 in the absence of IPTG showed no h-SA secreted into the growth medium. When the clones described in Table 10 were grown in growth medium with bolus fed with 5 mM IPTG at 24 hour intervals a range of responses by the clones is exemplified by the data presented in Table 11 with relative (to the control CLD446). Up to >100 fold increase in relative productivity was demonstrated vs. the control system (CLD446). Clone NRRL11430pAVE506-10 which demonstrated no h-SA secretion in the absence of IPTG showed a dramatic increase in productivity with a >>1000 fold increase (Table 12). Other clones demonstrated fold increases of between ca. 1.2-24 (Table 12).

EXAMPLE 14

In order to first confirm integration and expression of *S. cerevisae* Mig1 protein in *Komagataella* hosts, vector pAVE359 (*S. cerevisiae* Mig1) was transformed into recombinant *Komagataella* strain NRRL11430 to generate clone NRRL11430pAVE359. pAVE359 was also cloned into CLD446 to generate clone CLD446pAVE359. Clones were examined for the expression of Mig1 protein by subjecting whole cell lysates to SDS-PAGE followed by Western blot (anti-Mig1 antibody) as is well established in the art. Western blot analysis confirmed the expression and intracellular accumulation of *S. cerevisiae* Mig1 protein.

The invention claimed is:

1. A recombinant yeast of the genus *Komagataella* which has been transformed with a galactose promoter and comprises an expression cassette for *S. cerevisiae* Mig1 protein.

2. The yeast according to claim 1, wherein the galactose promoter is selected from the *S. cerevisiae* GAL1 or GAL10 promoter.

3. The yeast according to claim 1 which has been transformed with both of *S. cerevisiae* GAL1 and GAL10 promoters.

4. The yeast according to claim 1, wherein the yeast has been transformed with a *S. cerevisiae* GAL4 regulon.

5. The yeast according to claim 1, wherein the yeast is *Komagataella phaffii*.

6. A process of producing a recombinant polypeptide which comprises expressing an expression cassette for the recombinant polypeptide in a recombinant yeast of the genus *Komagataella* which has been transformed with a galactose promoter and comprises an expression cassette for *S. cerevisiae* Mig1 protein, wherein the expression cassette is operably linked to the galactose promoter.

7. A process of producing a recombinant polypeptide which comprises expressing an expression cassette for the recombinant polypeptide in a methylotrophic yeast wherein the expression cassette is operably linked to a GAL10 promoter, and the methylotrophic yeast comprises an expression cassette for *S. cerevisiae* Mig1 protein.

8. The process according to claim 6, wherein the galactose promoter is selected from the *S. cerevisiae* GAL1 or GAL10 promoter.

9. The process according to claim 6, wherein the yeast has been transformed with both of *S. cerevisiae* GAL1 and GAL10 promoters.

10. The process according to claim 6, wherein the yeast has been transformed with a *S. cerevisiae* GAL4 regulon.

11. The process according to claim 6, wherein the yeast is *Komagataella phaffii*.

12. The process according to claim 9, wherein the yeast has been transformed with a *S. cerevisiae* GAL4 regulon.

13. The process according to claim 12, wherein the yeast is *Komagataella phaffii*.

14. The process according to claim 7, wherein the yeast has been transformed with both of *S. cerevisiae* GAL1 and GAL10 promoters.

15. The process according to claim 7, wherein the yeast has been transformed with a *S. cerevisiae* GAL4 regulon.

16. The process according to claim 14, wherein the yeast has been transformed with a *S. cerevisiae* GAL4 regulon.

* * * * *